US010405539B2

(12) United States Patent
Mitter et al.

(10) Patent No.: US 10,405,539 B2
(45) Date of Patent: Sep. 10, 2019

(54) COMPOSITION

(71) Applicant: THE UNIVERSITY OF QUEENSLAND, St Lucia, Queensland (AU)

(72) Inventors: Neena Mitter, Seventeen Mile Rocks (AU); Zhi Ping Xu, Westlake (AU)

(73) Assignee: THE UNIVERSITY OF QUEENSLAND, Brisbane (AU)

(*) Notice: Subject to any disclaimer, the term of this patent is extended or adjusted under 35 U.S.C. 154(b) by 0 days.

(21) Appl. No.: 15/737,539

(22) PCT Filed: Jun. 17, 2016

(86) PCT No.: PCT/AU2016/050517
§ 371 (c)(1),
(2) Date: Dec. 18, 2017

(87) PCT Pub. No.: WO2016/201523
PCT Pub. Date: Dec. 22, 2016

(65) Prior Publication Data
US 2018/0177185 A1 Jun. 28, 2018

(30) Foreign Application Priority Data
Jun. 19, 2015 (AU) ................................ 2015902373

(51) Int. Cl.
| A61K 48/00 | (2006.01) |
| C07H 21/02 | (2006.01) |
| C07H 21/04 | (2006.01) |
| A01N 25/22 | (2006.01) |
| A01N 57/16 | (2006.01) |
| C12N 15/11 | (2006.01) |
| A01N 25/08 | (2006.01) |
| C12N 15/113 | (2010.01) |

(52) U.S. Cl.
CPC ............ *A01N 25/22* (2013.01); *A01N 25/08* (2013.01); *A01N 57/16* (2013.01); *C12N 15/111* (2013.01); *C12N 15/113* (2013.01); *C12N 2310/14* (2013.01); *C12N 2310/3511* (2013.01); *C12N 2320/32* (2013.01); *C12N 2320/51* (2013.01)

(58) Field of Classification Search
CPC .... C12N 15/113; C12N 15/111; A61K 31/713
See application file for complete search history.

(56) References Cited

U.S. PATENT DOCUMENTS

| 2005/0244439 | A1 | 11/2005 | Bringley |
| 2007/0117187 | A1 | 5/2007 | Ringerike et al. |
| 2009/0010888 | A1 | 1/2009 | Paine et al. |
| 2009/0108233 | A1 | 4/2009 | Lu et al. |
| 2009/0238805 | A1 | 9/2009 | Raemaekers et al. |
| 2014/0150134 | A1 | 5/2014 | Li et al. |
| 2015/0366979 | A1 | 12/2015 | Kost et al. |
| 2016/0138028 | A1* | 5/2016 | Kunos et al. ......... C12N 15/111 |
| 2017/0029819 | A1 | 2/2017 | Mitter et al. |
| 2018/0037907 | A1* | 2/2018 | Avisar et al. ...... C12N 2310/11 |

FOREIGN PATENT DOCUMENTS

| EP | 1911100 A2 | 3/2002 |
| WO | 03/004649 | 1/2003 |
| WO | WO-2004032862 A2 | 4/2004 |
| WO | WO-2004072267 A2 | 8/2004 |
| WO | 2006/045590 | 5/2006 |
| WO | WO-2008058342 A1 | 5/2008 |
| WO | WO-2008109142 A2 | 9/2008 |
| WO | WO-2008129060 A2 | 10/2008 |
| WO | WO-2011017137 A2 | 2/2011 |
| WO | 2012/126276 | 9/2012 |
| WO | WO-2014047623 A1 | 3/2014 |
| WO | WO-2014113423 A1 | 7/2014 |
| WO | WO-2014122648 A1 | 8/2014 |
| WO | WO-2015010026 A2 | 1/2015 |

OTHER PUBLICATIONS

Baum et al. (Nat Biotechnol., 2007, 25:1322-1326).*
Wu et al. (Journal of Biomaterials Applications, 2014, vol. 28(8), 1180-1189).*
International Search Report for PCT/AU2016/050517, dated Sep. 13, 2016, 3 pages.
Written Opinion of the ISA for PCT/AU2016/050517 dated Sep. 13, 2016, 5 pages.
Zhang, X. et al., "Chitosan/double-stranded RNA nanoparticle-mediated RNA interference to silence chitin synthase genes through larval feeding in the African malaria mosquito (*Anopheles gambiae*)", Insect Molecular Biology, 2010, vol. 19 (5), pp. 683-693.
Zhou, J., et al., "Nanoparticle-based delivery of RNAi therapeutics: progress and challenges", Pharmaceuticals, 2013, vol. 6, pp. 85-107.
Yu, N., et al., "Delivery of dsRNA for RNAi in insects: an overview and future directions", Insect Science, 2013, vol. 20, pp. 4-14.
He, B., et al., "Fluorescent nanoparticle delivered dsRNA toward genetic control of insect pests", Advanced Materials, 2013, vol. 25, pp. 4580-4584.
Allen and Walker, "Saliva of Lygus lineolaris digests double stranded ribonucleic acids", Journal of Insect Physiology, 2012, vol. 58, pp. 391-396.
Tenllado, F. & J.R. Diaz-Ruiz, "Double-stranded RNA-mediated interference with plant virus infection", Journal Virology, 2001, vol. 75, pp. 12288-12297.

(Continued)

*Primary Examiner* — Amy H Bowman
(74) *Attorney, Agent, or Firm* — Nixon & Vanderhye P.C.

(57) ABSTRACT

In one aspect, the present invention relates to a composition for delivery of double stranded RNA to an insect having a basic pH within its alimentary canal, wherein the composition comprises double stranded RNA adsorbed onto a clay complex, and wherein the clay complex is configured to release the double stranded RNA at the basic pH. Other aspects of the invention relate to preparations including the composition of the invention, methods of delivering double stranded RNA to an insect and methods of protecting a crop against an insect.

21 Claims, 8 Drawing Sheets
Specification includes a Sequence Listing.

(56) References Cited

OTHER PUBLICATIONS

Whyard et al., "Ingested double stranded RNAs can act as species-specific insecticides", Insect Biochemistry and Molecular Biology, 2009, vol. 39, pp. 824-832.
International Search Report for PCT/AU2014/000255, three pages (dated May 2014).
Written Opinion of the ISA for PCT/AU2014/000255, four pages (dated May 2014).
Int'l Preliminary Report on Patentability for PCT/AU2016/050517, six pages (dated Dec. 2017).
EPO supplementary search report for related EP 14870784, 11 pages (dated Sep. 2017).
Allen & Walker "Saliva of Lygus lineolaris digests double stranded ribonucleic acids" J. Insect Physiol. 58:391-396 (2012).
Bartel "MicroRNAs: Genomics, biogensis, mechanism and function" Cell 116:281-297 (2004).
Baulcombe "RNA silencing in plants" Nature 431:356-363 (2004).
Bin Hussein et al. "Controlled release of a plant growth regulator, α-naphthaleneacetate from the lamella of Zn—Al-layered double hydroxide nanocomposite" J. Controlled Release 82:417-427 (2002).
Brosnan et al. "Nuclear gene silencing directs reception of long-distance mRNA silencing in *Arabidopsis*" Proc. Natl. Acad. Sci. USA 104:14741-14746. (2007).
Chen et al. "Reduction of the size of layered hydroxide nanoparticles enhances the efficiency of siRNA delivery" J. Colloid Interface Sci. 390:275-281 (2013).
Choy et al. "Clay minerals and layered double hydroxides for novel biological applications" Appl. Clay Sci. 36:122-132 (2007).
Dean et al. "Top 10 fungal pathogens in molecular plant pathology" Mol. Plant Pathol. 13:414-430 (2012).
Dietzgen & Mitter "Transgenic gene silencing strategies for virus control" Australasian Plant Pathol. 35:605-618 (2006).
Duan et al. "Overexpression of the wild potato eIF4E-1 variant Eva1 elicits Potato virus Y resistance in plants silenced for native eIF4E-1" Transgenic Res. 21:929-938 (2012).
Dubey et al. "Controlled release agrochemicals formulations: A review" J. Sci. Indust. Res. 70:105-112 (2011).
Gan et al. "Bacterially expressed dsRNA protects maize against SCMV infection" Plant Cell Rep. 29:1261-1268 (2010).
Gardner et al. "Direct synthesis of aloxide-intercalated derivatives of hydrotalcite-like layered double hydroxides: Precursors for the formation of colloidal layered double hydroxide suspensions and transparent thin films" Adv. Mater. 13:1263-1266 (2001).
Ghormade et al. "Perspective for nano-biotechnology enabled protection and nutrition of plants" Biotech. Adv. 29:792-803 (2011).
Gleave "A versatile binary vector system with a T-DNA organisational structure conducive to efficient integration of cloned DNA into the plant genome" Plant Mol. Biol. 20:1203-1207 (1992).
He et al. "Fluorescent nanoparticle delivered dsRNA toward genetic control of insect pests" Adv. Mater. 25:4580-4584 (2013).
Karthikeyan et al. "RNA interference: Evolutions and applications in plant disease management" Arch. Phytopathol. Plant Protection 46:1430-1441 (2013).
Ladewig et al. "Controlled preparation of layered double hydroxide nanoparticles and their application as gene delivery vehicles" Appl. Clay Sci. 48:280-289 (2010).
Ladewig et al. "Efficient siRNA delivery to mammalian cells using layered double hydroxide nanoparticles" Biomaterials 31:1821-1829 (2010).
Lecellier & Voinnet "RNA silencing: No mercy for viruses?" Immunol. Rev. 198:285-303 (2004).
Lilley et al. "RNA interference in plant parasitic nematodes: A summary of the current status" Parasitol. 139:630-640 (2012).
Mills et al. "Nomenclature of the hydrotalcite supergroup: Natural layered double hydroxides" Mineralog. Mag. 76:1289-1336 (2012).
Mitter & Dietzgen "Use of hairpin RNA constructs for engineering plant virus resistance" Meth. Mol. Biol. 894:191-208 (2012).
Mitter et al. "Fate of hairpin transcript components during RNA silencing and its suppression in transgenic virus-resistant tobacco" J. Biotechnol. 126:115-122 (2006).
Mitter et al. "Cucumber mosaic virus infection transiently breaks dsRNA-induced transgenic immunity to Potato virus Y in tobacco" Mol. Plant Microbe Interact. 16:936-944 (2003).
Price & Gatehouse "RNAi-mediated crop protection against insects" Trends Biotechnol. 26:393-400 (2008).
Scholthof et al. "Top 10 plant viruses in molecular plant pathology" Mol. Plant Pathol. 12"938-954 (2011).
Tenllado & Diaz-Ruiz "Double-stranded RNA-mediated interference with plant virus infection" J. Virol. 75:12288-12297 (2001).
Tenllado et al. "Crude extracts of bacterially expressed dsRNA can be used to protect plants against virus infections" BMC Biotechnol. 3:3 (2003).
Timmons & Fire "Ingestion of bacterially expressed dsRNAs can produce specific and potent genetic interference in Caenorhabditis elegans" Gene 263:103-112 (2001).
Tyner et al. "Nanobiohybrids as delivery vehicles for camptothecin" J. Controlled Release 95:501-514 (2004).
Whyard et al. "Ingested double-stranded RNAs can act as species-specific insecticides" Insect Biochem. Mol. Biol. 39:824-832 (2009).
Wong et al. "Efficiency of layered double hydroxide nanoparticle mediated delivery of siRNA is determined by nucleotide sequence" J. Colloid Interface Sci. 369:453-459 (2012).
Wong et al. "Efficient delivery of siRNA to cortical neurons using layered double hydroxide nanoparticles" Biomaterials 31:8770-8779 (2010).
Xu & Lu "Layered double hydroxide nanomaterials as potential cellular drug delivery agents" Pure Appl. Chem. 78:1771-1779 (2006).
Yu et al. "Delivery of dsRNA for RNAi in insects: An overview and future directions" Insect Sci. 20:4-14 (2013).
Zhang et al. "Chitosan/double-stranded RNA nanoparticle-mediated RNA interference to silence chitin synthase genes through larval feeding in the African malaria mosquito (*Anopheles gambiae*)" Insect Mol. Biol. 19:683-693 (2010).
Zhou et al. "Nanoparticle-based delivery of RNAi therapeutics: Progress and challenges" Pharmaceuticals 6:85-107 (2013).
Allen et al. "Saliva of Lygus lineolaris digests double stranded ribonucleic acids" J. of Insect Physiology 58:391-396 (2012).
Arrowhead Research Corporation "About RNAi & the promise of siRNA therapeutics" (Oct. 1, 2014).
Asokan et al. "Response of various target genes to diet-delivered dsRNA mediated RNA interference in the cotton bollworm, *Helicoverpa armigera*" J. Pest. Sci. 87:163-172 (2014).
Borovsky "Insect peptide hormones and RNA-mediated interference (RNAi): Promising technologies for future plant protection" Phytoparasitica pp. 109-112 (2005).
Burand et al. "RNAi: Future in insect management" J. of Invertebrate Pathology 112:S68-S74 (2013).
Downes et al. "Incipient resistance of *Helicoverpa punctigera* to the Cry2Ab Bt Toxin in Bollgard II Cotton" PLOS One 5:1-5 (2010).
EPPO "Data sheets on quarantine pets: *Helicoverpa armigera*" pp. 1-6 (2014).
Fournier et al. "Tunable pH- and temperature-sensitive copolymer libraries by reversible addition-fragmentation chain transfer copolymerizations of methacrylates" Macromolecules 40:915-920 (2007).
Gong et al. "Silencing of Rieske iron—sulfur protein using chemically synthesised siRNA as a potential biopesticide against Plutella xylostella" Pest. Manag. Sci. 67:514-520 (2011).
Grayson "Acidity-alkalinity in the alimentary canal of twenty insect species" The Virginia J. of Science pp. 46-61 (1951).
Grayson "Digestive tract pH of six species of coleopteran" Annals Entomological Society of America 51:403-405 (1958).
Gu et al. "Recent advances in RNA interference research in insects: Implications for future insect pest management strategies" Crop Protection 45:36-40 (2013).
Insect management information for specific field crops Dept. of Agriculture, Fisheries and Forestry http://www.daff.qld.gov.au/site-map (2014).
Jayachandran et al. "An insect trypsin-like serine protease as a target of microRNA: Utilization of microRNA mimics and inhibitors by oral feeding" Insect Biochemistry and Molecular Biology 43:398-406 (2013).

(56) References Cited

OTHER PUBLICATIONS

Katoch et al. "Insect gut nucleases: a challenge for RNA interference mediated insect control strategies" International Journal of Biochemistry and Biotechnology 1:198-203 (2012).

Kumar et al. "Silencing of acetylcholinesterase gene of Helicoverpa armigera by siRNA affects larval growth and its life cycle" Journal of Insect Physiology 55:273-278 (2009).

Mendelsohn et al. "Are Bt crops safe?: The US EPA's analysis of Bt crops finds that they pose no significant risk to the environment or to human health" Nature Biotechnology 21:1003-1009 (2003).

Price et al. "RNAi-mediated crop protection against insects" Trends in Biotechnology 26:393-400 (2008).

"Pest Management R&D; Australia Northern Region" https://web.archive.org/web/20140707053903/http://www.daff.qld.gov.au/sitemap (2014).

Roignant et al. "Absence of transitive and systemic pathways allows cell-specific and isoform-specific RNAi in *Drosophila*" (2003).

Scott et al. "Towards the elements of successful insect RNAi" Journal of Insect Physiology 59:1212-1221 (2013).

Sharma et al. "Influence of transgenic cotton on the relative abundance and damage by target and non-target insect pests under different protection regimes in India" Crop Protection 25:800-813 (2006).

Sinha "The hydrogen-ion concentration in the alimentary canal of beetles infesting stored grain and grain products" Annals of the Entomological Society of America 52:763-765 (1959).

Siomi et al. "On the road to reading the RNA-interference code" Nature 457:396-404 (2009).

Sithanantham et al. "Plant protection in field crops: Insect pests of pigeonpea and chickpea and their management" Lead papers of the National Seminar on Plant Protection in Field Crops CPPTI, Hyderabad (Jan. 29-31, 1986).

Tabashnik et al. "Insect resistance to Bt crops: lessons from the first billion acres" Nature Biotechnology 31:510-521 (2013).

Terenius et al. "RNA interference in Lepidoptera: An overview of successful and unsuccessful studies and implications for experimental design" Journal of Insect Physiology 57:231-245 (2011).

Wang et al. "RNAi silencing of the HaHMG-CoA reductase gene inhibits oviposition in the *Helicoverpa armigera* cotton bollworm" PLOS One 8:1-9 (2013).

Xiong et al. "Silencing the HaHR3 gene by transgenic plant-mediated RNAi to disrupt *Helicoverpa armigera* development" International Journal of Biological Sciences 9:370-381 (2013).

Yang et al. "Efficiency of different methods for dsRNA delivery in cotton bollworm (*Helicoverpa armigera*)" Journal of Integrative Agriculture pp. 1-17 (2013).

Yu et al. "Delivery of dsRNA for RNAi in insects: an overview and future directions" Insect Science 20:4-14 (2013).

Zhang et al. "Feasibility, limitation and possible solutions of RNAi-based technology for insect pest control" Insect Science 20:15-30 (2013).

Int'l Preliminary Report on Patentability for PCT/AU2016/050517, six pages, dated Dec. 19, 2017.

Extended European Search Report dated Dec. 6, 2018 in European Patent No. 3322295.

* cited by examiner

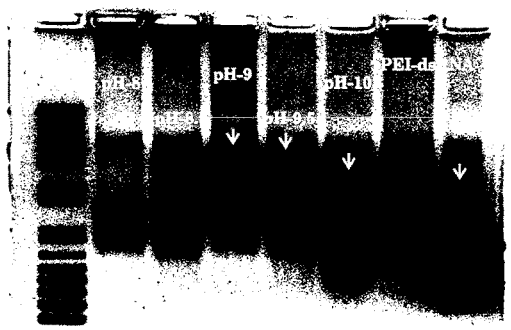 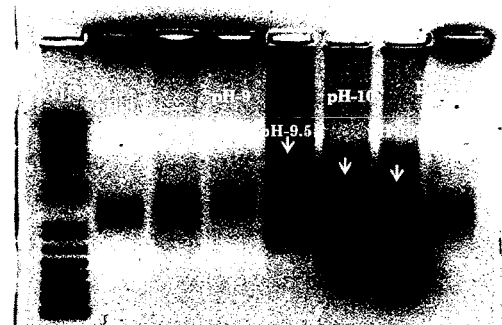
Figure 4A                    Figure 4B
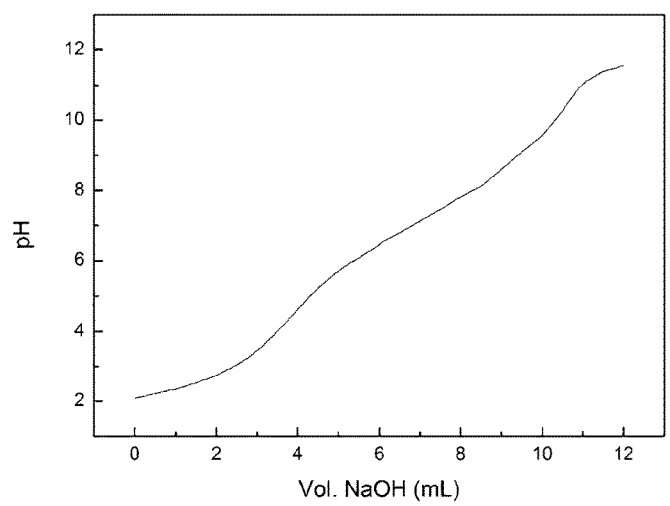
Figure 5
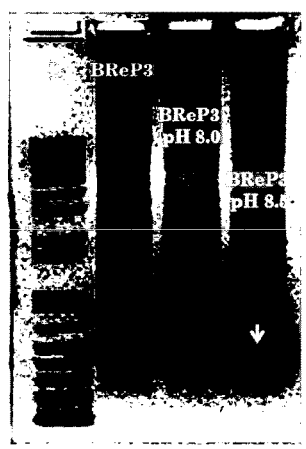 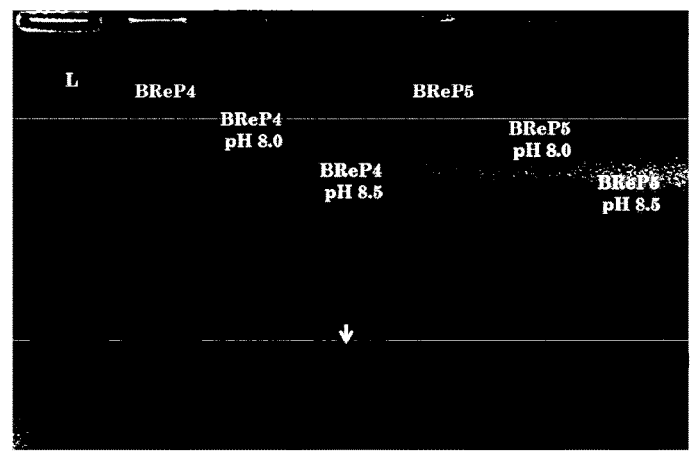
Figure 6A                    Figure 6B

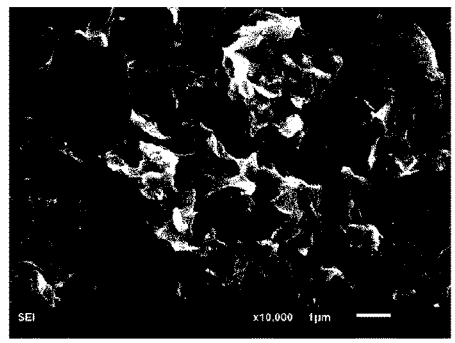
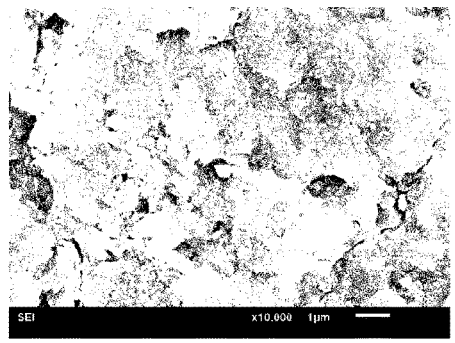
Figure 10A               Figure 10B
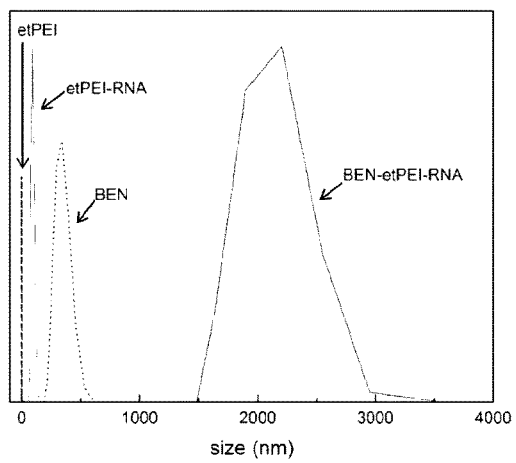
Figure 11
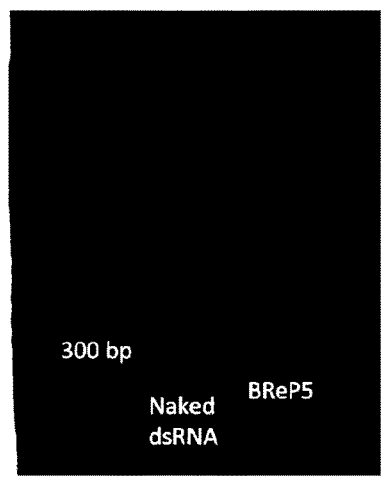
Figure 12

Loading of dsRNA

Release of dsRNA

COMPOSITION

This application is the U.S. national phase of International Application No. PCT/AU2016/050517 filed 17 Jun. 2016, which designated the U.S. and claims priority to AU Patent Application No. 2015902373 filed 19 Jun. 2015, the entire contents of each of which are hereby incorporated by reference.

TECHNICAL FIELD

The present invention relates to, inter alia, compositions for insects, to methods of preparing such compositions, and to methods of using such compositions.

BACKGROUND ART

It will be clearly understood that, if a prior art publication is referred to herein, this reference does not constitute an admission that the publication forms part of the common general knowledge in the art in Australia or in any other country.

The discussion below especially relates to the protection of plants against insect populations, and especially the control of insect populations that eat plants. However, for the avoidance of doubt, the present invention is not limited to protection of plants or the control of such insect populations. For example, many of the issues with chemical agents for controlling insects discussed below are also of concern for non-agricultural insect control.

Two of the most common strategies for the control of insect pests on plants include breeding for disease resistance and chemical control. Chemical control in particular is frequently used to control insect populations, but chemical agents are often expensive. Furthermore, there are safety concerns relating to the potential impact of chemical agents on the environment and the use of chemical agents on, for example, fruits and vegetables to be consumed by people. These last issues are factors that have contributed to the growth of the market for organic fruit and vegetables.

A further critical factor is that insects can and have developed resistance to traditional chemical agent insecticides. For example, in Australia field populations of insecticide-resistant *Helicoverpa armigera* (Cotton bollworm) have developed, and these resistant sub-types represent a significant pest in Australia's northern grain region (which encompasses all of Queensland's production areas). Crops affected by *H. armigera* include canola, chickpea, cotton, lucerne, maize, millets and panicums, mungbeans, peanuts, sorghum, soybeans, sunflowers and winter cereals including wheat, barley, oats, canary and triticale. *H. armigera* is also a major agricultural pest endemic to Europe, Asia and Africa. It is highly polyphagous and has been shown to feed on greater than 180 species of plant in 47 families. *H. armigera* has been estimated to cause US$2 billion in crop damage annually, despite the expenditure of US$500 million worth of pesticides for its control. However, *H. armigera* is just one species in the order of Lepidoptera, which is the second largest insect order comprised of moths and butterflies. The larval stage of moths cause major damage to many economically valuable crops including cotton, tobacco, tomato, corn, sorghum, lucerne, sunflower, pulses and wheat.

One effort to reduce the use of chemical insecticides on plants has involved the development of transgenic plants. For example, over the last two decades there has been an increase in the adoption of transgenic plants expressing insecticidal proteins encoded by genes from the bacterium *Bacillus thuringiensis* (Bt). However, the availability of suitable plants is limited, and sub-types of *H. armigera*, for example, have developed resistance to both single and dual-toxin forms of Bt cotton. Furthermore, large-scale application of transgenic plants has encountered resistance from the public and from regulatory agencies, and the cost, laboriousness and time needed to develop transgenic plants makes this an unattractive option.

RNAi, or RNA interference (also known as RNA silencing), has been used for genetic research in insects and it has promise in entomology as it provides target-specific silencing of gene expression. However, there are many difficulties in using RNAi to control the impact of insect pests on plants.

The RNAi mechanism involves first introducing double stranded RNA (dsRNA) into the insect haemocoel (for example via ingestion/injection/soaking), after which the dsRNA proceeds to enter the insect cells via endocytosis or via transmembrane proteins. Next, dsRNA is digested within the insect cells by a ribonuclease III (RNaseIII) enzyme known as Dicer into short interfering RNAs (siRNAs) of 20-25 nucleotides in length. The siRNAs are then unwound and one strand (the guide strand) is loaded into the RNA induced silencing complex (RISC). Lastly, the RISC locates and binds to messenger RNAs (mRNAs) containing sequences complementary to the guide strand, resulting in degradation of mRNA of the target gene, finally leading to the death of the cell.

A major difficulty in using the RNAi mechanism is how to effectively deliver dsRNA to insects. In particular, most laboratory studies of RNAi in insects have utilised microinjection of in vitro synthesised dsRNAs into embryos or the hemocoel. Clearly, however, microinjection as a delivery mechanism is not feasible for large-scale plant protection. Another strategy is for insects to ingest the dsRNA by providing it mixed in the diet, but this means that the dsRNA enters the insect alimentary canal, and especially the midgut. The environment of the midgut is hostile to dsRNA, due to the pH of the midgut and the presence of gut nucleases. Nucleases capable of degrading dsRNA may also be present in the saliva of insects (as recently reported for the tarnished plant bug *Lygus lineolaris* by Allen and Walker (2012) Saliva of *Lygus lineolaris* digests double stranded ribonucleic acids. Journal of Insect Physiology, 58, 391-396). Furthermore, research indicates that systemic RNAi responses may be more robust in less derived insect species, but some more derived Dipteran and Lepidopteran species may be refractory to systemic RNAi.

Another difficulty is how to provide the dsRNA to insects for ingestion. dsRNA is vulnerable to nucleases in the environment, and also to ultraviolet light, specifically if it has to be provided as a topical application on the plant surface. For example, in one study dsRNA topically applied to a plant for protection against viruses could not protect the plants 7 days post application. Furthermore, when dsRNA was applied 24 hours after viral infection, the dsRNA was not able to protect the plants against the virus (Tenllado, F. & J. R. Diaz-Ruiz, (2001) Double-stranded RNA-mediated interference with plant virus infection. *Journal Virology* 75: 12288-12297). In another study, when dsRNA was added to insect foods, the dsRNA levels in different diets dropped by 14% in the solid foods for beetles and moths and by 32% in the aphid fluid diet after 3 days, and by 31% and 56% after 6 days, respectively (Whyard et al (2009) Ingested double stranded RNAs can act as species-specific insecticides. Insect Biochemistry and Molecular Biology, 39, 824-832).

Major challenges for application of RNAi to insects (after effective gene targets have been identified) are the stability of dsRNA prior to administration to the insect, and the delivery of dsRNA to the insect.

Consequently, there is a need to provide an effective alternative approach which allows for targeting of insect populations or an approach which at least partially overcomes at least one of the abovementioned disadvantages or which provides the consumer with a useful or commercial choice.

SUMMARY OF INVENTION

In a first aspect, the present invention provides a composition for delivery of dsRNA to an insect having a basic pH within its alimentary canal, wherein the composition comprises dsRNA adsorbed onto a clay complex, and wherein the clay complex is configured to release the dsRNA at the basic pH.

Advantageously, it has been found that when dsRNA is adsorbed onto the clay complex it is stable and the composition protects the dsRNA from UV light and from nucleases. The composition advantageously may be sprayed on crops, for example, to protect the crop against the insects. Furthermore, the dsRNA remains adsorbed on the clay complex until the composition encounters a basic pH, such as within the insects' alimentary canal. Without wishing to be bound by theory, it is expected that once in the insects' alimentary canal the dsRNA will be gradually released from the clay complex, which means that the composition provides a protective function for the dsRNA within the insect gut. When insecticidal dsRNA is used in a clay composition sprayed on plant leaves, it has been shown that a significant proportion of insects eating these leaves are adversely affected by the dsRNA or die.

The composition accordingly provides a system for delivery of dsRNA to insects having a basic pH within its alimentary canal. The dsRNA accordingly may be any suitable dsRNA for use with insects and need not be limited to insecticidal dsRNA. However, in one embodiment, the dsRNA adversely affects the insect, and is especially insecticidal dsRNA. In this embodiment, the composition may be an insecticidal composition. The composition may be for protecting plants. Insects may also be carriers for various diseases (such as malaria and dengue fever). The composition therefore may be for use in protecting humans and animals against disease.

As used herein, dsRNA that adversely affects an insect may include dsRNA that causes insect mortality or affects the normal function or behaviour of that insect or affects the physiological function of the insect, including sterilisation, viral infection and decreased mobility.

The composition may be suitable for any type of insect, as long as the insect has a basic pH within its alimentary canal. In one embodiment, the insect is a chewing or a biting insect. A chewing or biting insect will ingest the composition upon consuming a food coated with the composition. In another embodiment, the insect is of the order Diptera, Lepidoptera or Coleoptera. Exemplary insects include one or more of the following:

Insects of the order Diptera (especially flies, mosquitos, gnats or midges); especially insects of the family Tephritidae or Drosophilidae; more especially of the family Tephritidae; even more especially of the genus *Bactrocera* or *Vidalia*; most especially fruit flies;

Insects of the order Lepidoptera (especially moths or butterflies (including caterpillars)); especially:

Insects of the family Tortricidae, Noctuidae, Geometridae, Sesiidae, Sphingidae, Plutellidae or Pyralidae;

Insects of the family Noctuidae; especially of the genus *Helicoverpa*; most especially *Helicoverpa armigera* (Cotton bollworm); or Insects of the family Plutellidae; especially of the genus *Plutella*; most especially *Plutella xylostella* (Diamondback moth);

Insects of the order Coleoptera (especially example weevils or other beetles); especially insects of the superfamily Curculionoidea, more especially of the family Curculionidae, most especially weevils.

The insect may be an insect larvae (for example, for the order Lepidoptera the insect larvae may be a caterpillar). The insect may be a pest to plants (such plants may be as further defined below). In one embodiment, the insect is of the order Lepidoptera, especially of the family Noctuidae; especially of the genus *Helicoverpa*; most especially *Helicoverpa armigera*.

The insect has a basic pH within its alimentary canal. For the avoidance of doubt, reference herein to a pH within the alimentary canal of an insect does not mean that the entire alimentary canal has that pH. The insect may have a basic pH within one or more of its foregut (stomodeam), midgut (mesenteron) or hindgut (proctodeam); especially within the midgut. The basic pH may be a pH greater than 7.5, 8.0, 8.5, 9.0, 9.5, 10.0, 10.5 or 11.0. The basic pH may be a basic pH less than 11.0, 10.5, 10.0, 9.5, or 9.0. The basic pH may be a pH from 8.0 to 11.0, 8.5 to 11.0, 8.0 to 10.5, 9.0 to 10.0, 9.0 to 9.5, 9.0 to 10.5 or 9.0 to 11.0.

The composition may be a plant-protecting composition. The composition may be for protecting any suitable type of plant (or crop including a plurality of plants). The plant may be an embryophyte, especially a spermatophyte, more especially an angiosperm (such as a monocotyledon (or monocot), dicotyledon or eudicotyledon (eudicot)) or a gymnosperm.

Exemplary monocots include plants of the order: Asparagales (including Amaryllidaceae (such as leek, onion, garlic, shallots and chives) and Asparagaceae (such as asparagus)); Arecales (including Arecaceae (such as palms, for example coconut palm)); Dioscoreales (including Dioscoreaceae (such as yam)); Poales (including Bromeliaceae (such as pineapple) and Poaceae (including corn (maize), wheat, rice, barley, millet, sorghum, oats and bamboo)); and Zingiberales (including Musaceae (including banana) and Zingiberaceae (including ginger and galangal)).

Exemplary eudicots include plants of the order:

Apiales (including Apiaceae (such as parsnip, carrot and celery));

Asterales (including Asteraceae (such as lettuce, artichoke and sunflower));

Brassicales (including Brassicaceae (such as broccoli, cabbage, kale, cauliflower, brussel sprouts, bok choy, choi sum, kohlrabi, radish, turnip and rapeseed) and Capparaceae (such as capers));

Caryophyllales (including Amaranthaceae (such as spinach, chard and beet) and Polygonaceae (such as rhubarb));

Cucurbitales (including Cucurbitaceae (such as cucumber, squash, pumpkin, rockmelon, honeydew melon, zucchini and watermelon));

Ericales (including Actinidiaceae (such as kiwifruit) and Ericaceae (such as blueberry));

Fabales (including Fabaceae (such as various beans, pea, soy bean, mung bean, lentil, peanut and alfalfa (lucerne)));

Lamiales (including Oleaceae (such as olive));
Malpighiales (including Linaceae (such as flax));
Malvales (including Malvaceae (such as cotton));
Myrtales (including Myrtaceae (such as guava));
Rosales (including Cannabaceae (such as hemp), Rosaceae (such as strawberry, apple, pear, apricot, plum, cherry, peach, raspberry, almond, and nectarine) and Moraceae (such as fig));
Sapindales (including Rutaceae (such as citrus, for example orange, lemon, grapefruit, lime and mandarin) and Sapindaceae (such as lychee));
Solanales (including Convolvulaceae (such as sweet potato) and Solanaceae (such as potato, tomato, eggplant, peppers (such as *capsicum*) and tobacco)); and
Vitales (including Vitaceae (such as grape)).

In one embodiment, the composition is for protecting commercial agricultural crops. Exemplary crops include cereals, vegetables (including roots and tubers), fruits, pulses, oilcrops and fibre crops. Cereals may include corn (maize), rice, wheat, barley, sorghum, millet and oats. Vegetables may include broccoli, cauliflower, cabbage, artichokes, capers, kale, spinach, lettuce, bok choy, chard, choi sum, leeks, brussel sprouts, kohlrabi, galangal, ginger, celery, rhubarb, asparagus, bamboo shoots, potatoes, sweet potatoes, yams, soybeans, mung beans, alfalfa, carrots, parsnips, beets, radishes, turnips, onions, shallots and garlic. Fruits may include tomatoes, grapes, kiwifruit, berrys (including strawberrys, blueberrys and rasberrys), guava, pears, melons (including rockmelons, watermelons and honeydew melons), citrus (including oranges, mandarins, lemons, limes and grapefruits), stonefruit (including apricots, nectarines, plums, cherries and peaches), lychees, pineapples, figs, apples, bananas, cucumbers, squash, zucchinis, pumpkins, peppers, eggplants and avocados. Pulses may include beans, peas and lentils. Oilcrops may include crops from which oil may be obtained, such as palms, soybeans, rapeseeds, sunflower seeds, peanuts, cottonseeds, palm kernels, coconuts and olives. Fibre crops may include cotton, flax, hemp and bamboo. The crop may also be tobacco or a flowering plant.

The dsRNA may be plant-protecting dsRNA (or crop-protecting dsRNA). The plant-protecting double-stranded RNA (dsRNA) may be capable of protecting a plant (especially via RNA interference) against insects. Similarly, the crop-protecting dsRNA may be capable of protecting a crop against insects. The dsRNA may be insecticidal dsRNA. Insects may be as described above.

A specific dsRNA sequence may be selected based on the insect against which protection is sought, and an appropriate sequence may be readily selected by a skilled person.

Advantageously, in order for RNA interference to occur, the RNA nucleotide sequence must match the insect perfectly. Consequently, the dsRNA is likely to be highly specific to the target insect, limiting the possibility of adverse effects on predators to the insect, on the environment or on people at the time of consumption (in the case of vegetables and fruits, for example).

As used herein, the term "plant protecting", "crop protecting" and the like means that the composition/dsRNA is able to prevent or ameliorate the impact of an insect on a plant or crop. For example, dsRNA which protects a plant or crop against an insect may kill the insect, adversely affect the insect, or may deter the insect from feeding on the plant or crop.

The length of the dsRNA may vary depending on the insect(s) against which protection is sought. Advantageously, RNases in insects (Dicer-Like enzymes) will cleave long dsRNA sequences into much smaller fragments, each of which is typically 20-25 nucleotides in length. Therefore, long dsRNA sequences of, for example, 100 to 3000 base pairs may be used, and these longer sequences would be cleaved into such smaller fragments by the insect after the insect ingests the dsRNA. It is believed that these smaller nucleotide fragments (e.g. 21 nucleotides) are involved in the RNA interference mechanism.

A single dsRNA construct may be engineered by combining specific sequences from multiple insects or genetic targets which could target multiple organisms or genetic targets (including multiple genetic targets for the same insect), as each insect will cleave the dsRNA sequence into shorter fragments. For example, a single dsRNA construct could be used to target three different insects or genetic targets. The dsRNA may target at least two insects or genetic targets, more especially from 2 to 10 insects or genetic targets, even more especially from 4 to 8 insects or genetic targets.

The dsRNA may therefore be from 20 or 21 to 3000 base pairs in length; especially from 21 to 2500, or from 21 to 2000 base pairs in length; more especially from 80 to 1750, from 80 to 1500, or from 80 to 1200 base pairs in length; most especially from 100 to 1200, or from 250 to 1200 base pairs in length. Advantageously, use of such longer dsRNA sequences provides a much greater likelihood of the sequence being cleaved to a nucleotide sequence that will match with the desired insect to affect (e.g. kill) the insect. Also, it may be less expensive to produce one longer dsRNA construct that targets multiple insects or multiple genetic targets, rather than making individual constructs and formulations. Therefore, the dsRNA may be a dsRNA construct that targets multiple insects or multiple genetic targets (for example within a single insect).

Alternatively, the dsRNA may be a plurality of dsRNAs (or two or more dsRNAs). Each dsRNA sequence in said plurality of dsRNAs may have a different genetic target, target a different insect or target a combination of different genetic targets/insects. Consequently, in one embodiment the dsRNA is a plurality of dsRNAs for targeting a plurality of insects or genetic targets.

It is expected that the clay complex is able to adsorb dsRNA sequences of a variety of lengths regardless of the sequence.

In one embodiment, the dsRNA targets the electron transport chain (ETC) of an insect, especially the Rieske gene of an insect. In another embodiment, the dsRNA targets a voltage-dependent channel of an insect, especially a voltage-dependent anionic channel (VDAC) of an insect, more especially a VDAC in the mitochondrial outer membrane of an insect. In another embodiment, the dsRNA targets the muscles of an insect, especially the Arginine Kinase (AK) gene and SERCA (sarco/endoplasmic reticulum $Ca^{2+}$-ATPase) gene of an insect. The AK gene is mainly involved in energy metabolism whereas the SERCA gene is involved in calcium uptake in the endoplasmic reticulum. In another embodiment, the dsRNA targets a gut of an insect, especially the Glutathione Transferase (GTT) gene of an insect. The GTT gene is important in the detoxification of compounds. In another embodiment, the dsRNA targets the body wall and appendages of an insect, especially the Acetylcholinesterase (AchE) gene of an insect. The AchE gene is important in growth and development. In another embodiment, the dsRNA targets an intracellular receptor of an insect, especially the methoprene-tolerant (Met) receptor of an insect. In another embodiment, the dsRNA targets a GTPase hydrolase enzyme of an insect, especially the Rab4b GTPase of an insect. In another embodiment, the dsRNA targets a juvenile hormone esterase of an insect. In another embodiment, the dsRNA targets the mitochondria of an insect, especially the NV2 gene of an insect. The NV2 gene plays an important role in the electron transport chain (ETC). In another embodiment, the dsRNA targets the gut of an insect, especially the foregut of an insect, more especially the prophenoloxidase gene of an insect. The prophenoloxidase gene is involved in detoxification of compounds. In another embodiment, the dsRNA targets the cuticle and epidermis of an insect, especially the cathepsin L gene of an insect. The cathepsin L gene plays an important role in the moulting process.

Therefore, in one embodiment the dsRNA targets at least one of the group consisting of: the electron transport chain (ETC) of an insect, a voltage-dependent channel of an insect, a muscle of an insect, a gut of an insect, a body wall and/or appendages of an insect, an intracellular receptor of an insect, a GTPase hydrolase enzyme of an insect, a juvenile hormone esterase of an insect, the mitochondria of an insect, and the cuticle and/or epidermis of an insect.

In another embodiment, the dsRNA includes a strand (antisense or sense) which is complementary to or at least partly complementary to a sequence as set forth in any one of SEQ ID NOs. 1, 2 and 4-14; more especially SEQ ID NOs. 1 or 2. As used herein, a strand which is "at least partly complementary" means that one strand of the dsRNA has at least 50%, at least 55%, at least 60%, at least 65%, at least 70%, at least 75%, at least 80%, at least 85%, at least 90%, or at least 91%, 92%, 93%, 94%, 95%, 96%, 97%, 98% or 99% sequence identity with the sequence. It would be appreciated that this definition takes into account that RNA uses a U instead of a T, as found in DNA.

In a further embodiment, at least a portion of a strand of the dsRNA (antisense or sense) is complementary to or at least partly complementary to a sequence as set forth in any one of SEQ ID NOs. 1, 2 and 4-14; more especially SEQ ID NOs. 1 or 2. As used herein, at least a portion of a strand which is "at least partly complementary" means that at least a portion of one strand of the dsRNA has at least 50%, at least 55%, at least 60%, at least 65%, at least 70%, at least 75%, at least 80%, at least 85%, at least 90%, or at least 91%, 92%, 93%, 94%, 95%, 96%, 97%, 98% or 99% sequence identity with the sequence. It would be appreciated that this definition takes into account that RNA uses a U instead of a T, as found in DNA.

In a further embodiment, the dsRNA includes or includes at least a portion of a strand (antisense or sense) which is complementary to or at least partly complementary to a fragment of a sequence as set forth in any one of SEQ ID NOs. 1, 2 and 4-14; more especially SEQ ID NOs. 1 or 2. By way of example only, a fragment may include at least 5%, 10%, 15%, 20%, 25%, 30%, 35%, 40%, 45%, 50%, 55%, 60%, 65%, 70%, 75%, 80%, 85%, 90% or 95% of a sequence which is complementary to or at least partly complementary to a sequence as set forth in any one of SEQ ID NOs. 1, 2 and 4-14; more especially SEQ ID NOs. 1 or 2.

The dsRNA may be produced in any suitable way. For example, the dsRNA may be produced in vitro via a kit, in vitro or in vivo via a bacteriophage (such as via a *Pseudomonas syringae* dsRNA bacteriophage), or in vivo using a specialised strain of organism, especially using a bacteria (such as a strain of *E. coli*). Typically, in vitro methods are suitable for smaller scale dsRNA production. For large scale production, in vivo production methods are preferred. The dsRNA used may be a crude bacterial extract.

The dsRNA may be in any suitable form and be of any suitable sequence. The dsRNA may include any suitable modifications. For example, the dsRNA may include one or more modified phosphate groups, modified nucleic acids/nucleotides, modified sugars and/or modified 5 or 3 prime ends. Exemplary modified groups which may be present in the dsRNA include, for example, inosine, methylinosine, pseudouridine, morpholine, locked nucleic acids, peptides (such as peptide nucleic acids (PNA)), biotin, cholesterol, fluorophores, radionuclides and metals. The dsRNA may also be in the form of a dsRNA construct. Such modifications may enhance the stability and/or longevity of the dsRNA.

The clay complex may include a clay. The clay may be an anionic clay. The clay may include a plurality of positively charged layers or sheets. However, in a preferred embodiment the clay is a cationic clay. The clay may include a plurality of negatively charged layers or sheets. The clay may be a silica-based clay. The clay may be a swelling clay. The clay may be bentonite. The clay may include, consist essentially of, or consist of montmorillonite.

The clay may have a charge density of from 10 to 400 millimolar equivalent charge per 100 g of clay (meq/100 g), especially a charge density of from 20 to 300 meq/100 g, more especially a charge density of from 30 to 250, from 40 to 200, from 50 to 200, from 70 to 150, from 80 to 120, from 90 to 110, or about 100 meq/100 g.

The clay may include a plurality of clay particles. The clay particles may have a z-average value of the particle size of up to 5 µm, more especially up to 1 µm, most especially up to 750 nm or up to 500 nm. In one embodiment, the clay particles may have a z-average value of the particle size of within the range 20-800 nm, more especially 100-800 nm or 250-650 nm, even more especially about 450 nm.

When the clay includes a plurality of negatively charged layers or sheets a further positively charged component is needed to enable the formation of a composition including both the clay and the dsRNA (as dsRNA carries a negative charge (due to the phosphate groups)).

Accordingly, in one embodiment, the clay complex includes a molecule having a plurality of positively charged groups (or a positively charged molecule), especially in a solution in which the pH is from 5.0 to 7.0. The molecule may be for complexing with a cationic clay and with dsRNA. The molecule may be adsorbed onto the clay. The molecule may be a macromolecule, especially a polymer. The molecule may be a dendrimer. The polymer may be a co-polymer or a block co-polymer.

The positive charge in the positively charged groups may be located (or at least partially located) on a nitrogen atom and/or a transition metal; especially a nitrogen atom.

The positively charged group may be a positively charged amine (including primary, secondary, tertiary, or quarternary amines), an imine (including primary and secondary imines), a guanidine group, or an aromatic amino group. Exemplary amines include alkylamine, alkylaminoalkyl or alkylamino(alkyl)alkyl (in which each alkyl group may be independently selected from $C_{1-12}$ alkyl, especially $C_{1-6}$ alkyl, more especially methyl, ethyl, propyl, butyl, pentyl or hexyl); and a nitrogen-containing saturated heterocyclic ring (examples include a nitrogen-containing saturated heterocyclic ring having from 1 to 10 carbon atoms; especially pyrrolidinyl, pyrazolidinyl, piperidinyl, morpholinyl and quinuclidinyl). Exemplary imines include an alkylimine and an alkyliminoalkyl (in which each alkyl group may be independently selected from $C_{1-12}$ alkyl, especially $C_{1-6}$ alkyl, more especially methyl, ethyl, propyl, butyl, pentyl or hexyl). An exemplary guanidine group is an alkylguanidino group ((in which the alkyl may be independently selected from $C_{1-12}$ alkyl, especially $C_{1-6}$ alkyl, more especially methyl, ethyl, propyl, butyl, pentyl or hexyl). Exemplary aromatic amino groups may include aromatic nitrogen containing heterocycles; especially aromatic nitrogen containing heterocycles having from 1 to 10 carbon atoms; more especially imidazolyl, triazolyl or purinyl. The molecule or positively charged groups may be optionally substituted with at least one (and especially a plurality) of pKa modifying groups, as described below. The pKa modifying groups may be geminal or vicinal to the positively charged groups (such as groups including nitrogen atoms) in the molecule.

As used herein, the term "alkyl" or "alkylene" refers to a straight chain or branched saturated hydrocarbon group. The alkyl group may have a specified number of carbon atoms, for example, $C_{1-12}$ alkyl refers to alkyl groups having 1, 2, 3, 4, 5, 6, 7, 8, 9, 10, 11 or 12 carbon atoms in a linear or branched arrangement. Unless otherwise defined, the term "alkyl" may be $C_{1-12}$alkyl or $C_{1-6}$alkyl. Examples of suitable alkyl groups may include, but are not limited to, methyl, ethyl, propyl (n-propyl and i-propyl), butyl (n-butyl, i-butyl and t-butyl), n-pentyl, 2-methylbutyl, 3-methylbutyl, 4-methylbutyl, 2-ethylpropyl, n-hexyl, 2-methylpentyl, methylpentyl, 4-methylpentyl, 2-ethylbutyl, 3-ethylbutyl, heptyl, octyl, nonyl, decyl, undecyl, dodecyl, cyclopentyl, cyclohexyl and cycloheptyl.

The molecule may be a molecule having a plurality of positively charged groups (or two or more positively charged groups), wherein the groups are selected from one or more of amine, imine, guanido, and aromatic amino groups. As used herein, the terms "positively charged groups", "positively charged molecule" or the like refer to a group or molecule with a positive charge at pH 5.0 to 7.0.

Without wishing to be bound by theory, it is believed that the composition may form through electrostatic interactions between, for example, a negatively charged clay, a positively charged molecule, and a negatively charged dsRNA. Consequently, if the positive charge of the positively charged groups in the molecule are neutralised (for example due to the basic pH within the insects' alimentary canal), the composition dissociates, releasing the dsRNA. Therefore, specific molecules having a plurality of positively charged groups may be selected for use with specific insects, and the pKa of the positively charged groups in the molecule can be manipulated or selected to control the release of dsRNA in the insect. By way of example, if the pH within an insects' alimentary canal is about 10.5, then a composition including a molecule with positively charged groups having a pKa of 9.0 would be expected to release dsRNA in the insects' alimentary canal more quickly and completely than a composition including a molecule with positively charged groups having a pKa of 10.5.

Accordingly, the pKa of the positively charged groups may be greater than 7.5, 8.0, 8.5, 9.0, 9.5, 10.0, 10.5 or 11.0. The pKa of the positively charged groups may be less than 11.0, 10.5, 10.0, 9.5, or 9.0. The pKa of the positively charged groups may be from 8.0 to 11.0, 8.5 to 11.0, 8.0 to 10.5, 9.0 to 10.0, 9.0 to 9.5, 9.0 to 10.5 or 9.0 to 11.0.

Furthermore, the dsRNA may be released from the composition at a pH of greater than 7.5, 8.0, 8.5, 9.0, 9.5, 10.0, 10.5 or 11.0. The dsRNA may be released from the composition at a pH of less than 11.0, 10.5, 10.0, 9.5, or 9.0. The dsRNA may be released from the composition at a pH of from 8.0 to 11.0, 8.5 to 11.0, 8.0 to 10.5, 9.0 to 10.0, 9.0 to 9.5, 9.0 to 10.5 or 9.0 to 11.0. If the pKa of the positively charged groups is, for example, 9.0, then it would be expected that dsRNA would be released from a composition including a molecule with those positively charged groups at a pH of 9.0.

The molecule having a plurality of positively charged groups may be of any suitable type. In one embodiment, the molecule is a polymer. The polymer may have a molecular weight of greater than 200, especially greater than 400, more especially greater than 600. The polymer may have a molecular weight of from 400 to 100,000, especially from 600 to 80,000. The polymer may have a molecular weight of from 10,000 to 50,000; especially from 10,000 to 40,000; most especially about 15,000 or about 33,000.

The polymer may be a co-polymer or a block co-polymer formed with at least one monomer providing at least one positively charged group. The polymer may also be a homopolymer, formed by only one monomer providing at least one positively charged group.

The polymer may have a plurality of positively charged nitrogen atoms (the positively charged groups may be positively charged nitrogen atoms). The pKa of the nitrogen atoms may be as described above for the positively charged groups. The polymer may be a branched or linear polymer. The polymer may be or include an optionally substituted polyalkyleneamine (may be known as polyalkyleneimine). An exemplary polyalkyleneamine may be polyhexyleneamine (may be known as polyhexyleneimine), polypentyleneamine (may be known as polypentyleneimine), polybutyleneamine (may be known as polybutyleneimine), polypropyleneamine (may be known as polypropyleneimine) or polyethyleneamine (may be known as polyethyleneimine); especially polyethyleneamine. Polyethyleneamine includes amino groups having pKa values from 10.5 to 11.0 and thus would be expected to release dsRNA at a pH of about or greater than 10.5.

The optional substituents for the polyalkyleneamine may be pKa modifying groups or a plurality of pKa modifying groups. Accordingly, the polymer may be a polyalkyleneamine substituted by a plurality of pKa modifying groups. The pKa modifying groups may be electron withdrawing groups or electron donating groups. The pKa modifying groups may be geminal or vicinal to the amine groups in the polymer. Exemplary electron withdrawing groups may include carbonyl-containing groups (such as esters (including —CO—O-alkyl groups) and carboxylic acids (including a —CO—OH group)), nitro groups, cyano groups, protonated amino groups (such as a tetra-alkyl substituted nitrogen) and sulfate groups. The pKa modifying groups may also include -alkyl, —OH, ethers (including —O-alkyl groups), and amines (including —NH— alkyl and —N(alkyl)-alkyl groups), in which the alkyl groups may be optionally substituted with one or more of —OH, —O-alkyl, -halo (including —F, —Cl, —Br of —I), —CO-alkyl, —CO—O-alkyl, —O—CO-alkyl, —NH-alkyl, —N(alkyl)$_2$, —CO—NH-alkyl and —NH—CO-alkyl.

In one embodiment, the polymer is a polyalkyleneamine substituted with pKa modifying groups geminal or vicinal to the amine groups in the polymer. The polymer may be a polyalkyleneamine substituted with hydroxyl groups or —O-alkyl groups vicinal to the amine groups in the polymer. The polymer may be ethoxylated polyethyleneamine. Ethoxylated polyethyleneamine includes amino groups having pKa values of about 9.0-9.5. For the avoidance of doubt, a polyalkyleneamine may include either or both of amine and imine groups. For example, ethoxylated polyethyleneamine may include one or more of the following units: —NH(CH$_2$CH$_2$OH), —N(CH$_2$CH$_2$OH)$_2$, and —N(CH$_2$CH$_2$OH)—.

The polymer may be polyalkylene-based; especially polyhexylene-based, polypentylene-based, polybutylene-based, polypropylene-based or polyethylene-based; most especially polyethylene-based. The polyalkylene-based polymer may include a positively charged group geminal or vicinal to a pKa modifying group (especially an electron withdrawing group). In one embodiment, the alkylene group (especially an ethylene group) in the polyalkylene-based polymer may be substituted by an amino group, and optionally vicinal to the amino group is an electron withdrawing group. The polymer may be polyethylene-based, wherein the ethylene group in the polyethylene-based polymer is substituted by an amino group and optionally substituted by an electron withdrawing group vicinal to the amino group. The amino group may be a dialkylamino group; more especially a diethylamino or dimethylamino group; most especially a dimethylamino group. The electron withdrawing group may be an alkyleneester (—R—COO—), alkyleneether (—R—O—) or alkylene-carbonyl (—R—CO—); more especially an ethylene-CO—O— group). The electron withdrawing group may be derived from a methacrylate. In an exemplary embodiment, the polymer may be or include a polydialkylaminoalkylmethacrylate. In a further exemplary embodiment, the polymer may be poly(2-dimethylaminoethyl methacrylate) (or pDMAEMA). pDMAEMA includes alkylated amino groups having pKa values of about 7.0-7.5. In another exemplary embodiment, the polymer may be poly(2-(diethylamino)ethyl methacrylate) (or pDEAEMA). pDEAEMA has similar pKa values to pDMAEMA.

The polymer may be a homopolymer, co-polymer or block co-polymer including a dialkylaminoalkylmethacrylate (such as a 2-(dimethylamino)ethyl methacrylate or DMAEMA). The co-polymer or block co-polymer including a dialkylaminoalkylmethacrylate may also include a second dialkylaminoalkylmethacrylate, a polyalkyleneoxide (such as polyethyleneoxide or PEO), or a polyalkylacrylamide (such as poly(N-isopropylacrylamide) or PNIPAM). Exemplary co-polymers or block co-polymers include pDMAEMA-pDEAEMA, pDMAEMA-PEO, and pDMAEMA-PNIPAM. In such polymers the pKa of the amino group may vary, allowing the dsRNA to be released at different pHs.

The composition may include up to 40 wt % dsRNA, especially up to 30 wt % dsRNA, more especially up to 25 wt % or 20 wt % dsRNA. The composition may include more than 0.5 wt % dsRNA; especially more than 1 wt % dsRNA, 2 wt % dsRNA, 3 wt % dsRNA, 4 wt % dsRNA or 7 wt % dsRNA; more especially more than 5 wt % dsRNA. The composition may include from 0.5 to 30 wt % dsRNA, from 1 to 30 wt % dsRNA, from 5 to 30 wt % dsRNA or from 5 to 20 wt % dsRNA; more especially from 5 to 25 wt % dsRNA or from 7 to 25 wt % dsRNA; most especially about 8 to 25 wt % dsRNA.

When a molecule having a plurality of positively charged nitrogen groups is present in the composition, the N:P ratio in the composition (i.e. the nitrogens in the molecule (N):the phosphorous in the dsRNA(P)) may be at least 1, 2, or 3, especially at least 4, more especially at least 5. The N:P ratio in the composition may be less than 30, less than 20, less than 10, or less than 7; especially less than 6. The N:P ratio in the composition may be from 3-7, especially from 4-6, more especially about 5.

In a composition in which the clay complex includes a clay and a molecule having a plurality of positively charged groups, the mass ratio of clay:molecule/dsRNA (or of clay:molecule) may be from 1:1 to 10:1, especially from 3:1 to 8:1, more especially from 4:1 to 7:1 or 5:1 to 7:1, most especially about 6:1 or about 5:1. The mass ratio of clay:molecule:dsRNA may be about 5:1:2.

Without wishing to be bound by theory, the loading ratio of different components in the composition may affect the release of dsRNA. For example, at the same basic pH a composition including a higher proportion of positively charged groups would be expected to release dsRNA more slowly than a composition including a lower proportion of positively charged groups (as the base has a greater amount of positive charges to neutralise).

In one embodiment, the composition has a z-average value of particle size of up to 5000 nm, especially up to 3000 nm, more especially of up to 2500 nm. In another embodiment, the composition has a z-average value of particle size of at least 50 nm, 100 nm, 250 nm or 500 nm, especially at least 1000 nm, more especially at least 1500 nm, most especially at least 2000 nm. In one embodiment, the composition has a z-average value of particle size of about 2100 nm. The composition may have a z-average value of particle size of from 50 nm to 5 μm, especially from 100 nm to 1 μm. The ideal particle size of the composition may vary depending on the food to which the composition is to be applied.

In another embodiment, the composition has a positive zeta potential, especially a zeta potential of greater than 0.5 mV. In another embodiment, the composition has a zeta potential of less than 25 mV, especially less than 15 mV, more especially less than 10 mV, even more especially less than 5 mV. In a further embodiment, the composition has a zeta potential of about 1.3 mV.

As used herein, the term "dsRNA adsorbed onto a clay complex" and the like includes circumstances in which dsRNA is adsorbed onto the surface of the clay complex, circumstances in which dsRNA is intercalated between clay complex layers, and circumstances in which dsRNA is adsorbed onto the molecule having a plurality of positively charged groups where the dsRNA/molecule is adsorbed on the surface of a clay or between clay layers. Therefore, the term "adsorbed" includes both adsorption onto the surface of the clay or clay complex, as well as intercalation between clay or clay complex layers.

Without wishing to be bound by theory, it is believed that when dsRNA is adsorbed onto the clay complex, the dsRNA is afforded some protection against RNases and U.V. light, and thus the dsRNA is significantly more stable. Thus, it is believed that the clay complex acts as a protective coating for the adsorbed dsRNA.

Advantageously, it is expected that when dsRNA is adsorbed onto the clay complex, the dsRNA substantially does not degrade, even when stored for more than 60 days. When the dsRNA is adsorbed onto the clay complex, the clay complex advantageously protects the dsRNA against RNase and UV light.

In a second aspect, the present invention relates to a preparation including the composition of the first aspect of the present invention. Context permitting, features of the second aspect of the present invention may be as described for the first aspect of the present invention.

The preparation may include one composition of the first aspect of the present invention, or a plurality of compositions of the first aspect of the present invention. For example, a user may be provided multiple compositions (for example in solid or powder form) which each target one insect pest. If the user wishes to target three insect pests when spraying a crop, for example, the user may mix three compositions and a fluid to prepare a single preparation for spraying.

The preparation may be in any suitable form. For example, the preparation may be in the form of a solid, ointment, gel, cream, powder, paste, suspension, colloid, foam or aerosol; especially a suspension or a colloid. Solid forms of the preparation may include dusts, powders, granules, pellets, pills, pastilles, tablets, filled films (including seed coatings) and the like, which may be water-dispersible ("wettable"). In one embodiment, the preparation is in the form of a concentrate, especially a concentrate in the form of a colloid or suspension.

In one embodiment the preparation is heterogeneous, especially comprising a solid phase dispersed within a fluid phase. The solid phase may comprise the composition. The fluid phase may be, for example, a liquid, a gas, or a free flowing solid, or a combination thereof; especially a liquid; more especially an aqueous liquid; most especially water. The water may be sterile or non-sterile. The solid-phase may be dispersed within the fluid phase in any suitable way. This will depend upon the nature of the solid-phase and the fluid-phase.

Depending on the form of the preparation, the preparation may include a variety of other agents. Exemplary agents include, but are not limited to, one or more of the following types of ingredients: diluents, carriers, excipients, suspension agents, agglomeration agents, bases, buffers, bittering agents, fragrances, preservatives, propellants, thixotropic agents, surfactants, anti-freezing agents, and colouring agents. Suitable agents may be selected by a skilled person.

The preparation may also include one or more other active ingredients. An active ingredient, as defined herein, is an ingredient that provides benefit to plant protection. The active ingredient may be, for example, an insecticide, a pesticide, a fungicide, an antibiotic, an insect attractant, an anti-parasitic agent, an anti-viral agent, or a nematicide.

When the preparation is in the form of a colloid or suspension, it may include the composition at up to 30% w/w, up to 20% w/w, up to 10% w/w, up to 5% w/w, up to 2% w/w, up to 1% w/w, less than 1% w/w, less than 0.1% (less than 1 mg/ml) or less than 0.01% w/w (less than 0.1 mg/ml). The preparation may be in a concentrated form which requires dilution prior to application to an insect food, plant or crop. The preparation for application to an insect food, plant or crop may include the composition at less than 1% w/w, less than 0.1% (less than 1 mg/ml) or less than 0.01% w/w (less than 0.1 mg/ml).

In another embodiment, when the preparation is in the form of a colloid or suspension, it may include the composition at up to 100 mg/L; especially up to 50 mg/L; more especially up to 20 mg/L or up to 10 mg/L; most especially less than 10 mg/L. In one embodiment, the concentration of the composition in a colloid or suspension is from 1-100 mg/L.

The preparation may be formulated for administration to a plant, or to any part of a plant, in any suitable way. For example, the preparation may be formulated for administration to the leaves, stem, roots, fruit, vegetables, grains and/or pulses of the plant. In one embodiment, the preparation is formulated for administration to the leaves of the plant, and is especially sprayable onto the leaves of the plant. The preparation may be sprayable onto the plant. The preparation may be administered to the plant as a metered dose. The preparation may be formulated for administration to the plant, for example, by spraying, by brush or by another applicator. The preparation may be formulated for administration to the plant by spraying (including via a fine mist), drip-feeding and/or irrigation.

The preparation may be in the form of a suspension, in which case the composition may be sprayable onto the plant. The suspension may be substantially stable. As used herein, a "substantially stable" suspension is a suspension in which, once formed, the solid phase remains sufficiently dispersed (i.e. does not significantly aggregate) in the fluid phase (especially a liquid phase, more especially water) for the suspension to be sprayed onto a plant. In one embodiment, the solid phase remains dispersed in the fluid phase for at least 24 hours after the suspension is formed, especially at least 5 days after the suspension is formed, more especially at least 10, 15, 20 or 30 days after the suspension is formed, most especially at least 60 days after the suspension is formed. If the suspension is not substantially stable, then the solid phase may aggregate leading to blockages in equipment when the suspension is sprayed onto plants, or alternatively leading to variable amounts of solid phase material being applied in a given area, resulting in incomplete protection for plants.

In a third aspect, the present invention provides a method of preparing the composition of the first aspect of the present invention. The method may include the step of adsorbing dsRNA onto a clay complex. The method may include the steps of: adsorbing a molecule having a plurality of positively charged groups onto a clay to form a clay complex; and adsorbing dsRNA onto the clay complex. The method may include the steps of adsorbing dsRNA onto a molecule having a plurality of positively charged groups; and adsorbing the dsRNA/molecule onto a clay.

Advantageously, it has been found that loading the dsRNA onto the molecule and then loading the dsRNA/molecule onto the clay provides significantly higher loading of dsRNA in the composition. Furthermore, this method also provides improved release parameters. In one embodiment, the molecule has a plurality of positively charged nitrogen groups. In this embodiment, in the dsRNA/molecule the N:P ratio (i.e. the nitrogens in the molecule (N):the phosphorous in the dsRNA(P)) may be at least 1, 2 or 3, especially at least 4, more especially at least 5. In this embodiment, in the dsRNA/molecule the N:P ratio may be less than 30, less than 20, less than 10, or less than 7, especially less than 6. In this embodiment, in the dsRNA/molecule the N:P ratio may be from 3-7, especially from 4-6, more especially about 5.

The step of adsorbing dsRNA onto the molecule may include contacting or incubating the dsRNA with the molecule in an aqueous solution with shaking or inversion. This step may be performed below 25° C., especially below 15° C., more especially below 10° C., most especially below 5° C. This step may be performed on ice. This step may be performed at about pH 7.

The step of adsorbing the dsRNA/molecule onto a clay may include contacting or incubating the dsRNA/molecule with the clay in an aqueous solution with shaking or inversion. This step may be performed below 25° C., especially below 15° C., more especially below 10° C., most especially below 5° C. This step may be performed on ice. This step may be performed at about pH 7. In one embodiment, the composition formed by the method includes a clay, a molecule having a plurality of positively charged groups, and dsRNA. In this embodiment, the mass ratio of clay:molecule/dsRNA (or of clay:molecule) may be from 1:1 to 10:1, especially from 3:1 to 8:1, more especially from 4:1 to 7:1 or from 5:1 to 7:1, most especially about 6:1 or about 5:1.

Features of the third aspect of the present invention may be as described above for the first aspect.

In a fourth aspect, the present invention relates to a method of delivering dsRNA to an insect having a basic pH within its alimentary canal, the method comprising administering (or applying) the composition of the first aspect or the preparation of the second aspect of the present invention to an insect food.

The composition may be administered to any insect food. Such foods may include plants and plant parts (including fruits and vegetables, for example), but also may include synthetic insect food sources, insect baits or water traps. In one embodiment, the insect food is a plant (including parts of plants). Advantageously, the insect may ingest the composition while ingesting the food. The step of administering the composition to an insect food may involve spraying, dripping or pouring the composition or preparation onto the food, or brushing the composition or preparation onto the food.

In a fifth aspect the present invention relates to a method of protecting a crop against an insect having a basic pH within its alimentary canal, the method comprising the step of administering (or applying) to a crop the composition of the first aspect or the preparation of the second aspect of the present invention. The crop may include a plurality of plants as defined above. The step of administering the composition or preparation to the crop may involve administering the preparation or composition to the leaves, stem, roots, fruit, vegetables, grains and/or pulses of the plants within the crop. The step may involve spraying the composition or preparation onto the crop, especially onto the leaves of the plants in the crop. The step may involve brushing the composition or preparation onto the crop, especially onto the leaves of the plants within the crop. The step may involve administering the composition or preparation to the crop by spraying, drip-feeding or irrigation.

In one embodiment of the fifth aspect the dsRNA is insecticidal dsRNA. In this embodiment, the composition is an insecticidal composition.

Features of the fourth and fifth aspects of the present invention may be as described for the first and second aspects of the present invention, context permitting.

In a sixth aspect, the present invention provides the composition of the first aspect, or a preparation of the second aspect, when applied to a plant. Features of the sixth aspect may be as described above for the first and second aspects.

Further features of the fourth to sixth aspects of the present invention may be as described below.

In one embodiment, the composition or preparation, once applied to a plant or crop, is capable of protecting the plant or crop for at least 15 days, especially at least 20 days, more especially at least 25 days, most especially at least 30 days. In a further embodiment, the composition, once administered to a plant or crop, is capable of protecting the plant or crop for from 2 to 8 weeks, especially from 3 to 6 weeks, most especially from 4 to 5 weeks. Once administered to a plant or crop, the composition may degrade at a rate of 10-30% per week, especially 15-25% per week, more especially at a rate of 15-20% per week. The duration of protection may be affected, for example, by the amount of rainfall on the plant or crop. Therefore, in a drier climate it is expected that the duration of protection would be increased, whereas a shorter duration of protection may be provided in a wetter climate.

The composition may also be administered to the plant or insect food at any suitable concentration, and advantageously the dsRNA in the composition may be effective at relatively low concentrations. In one embodiment, less than 100 µg of dsRNA per plant may be administered, especially less than 50 µg, more especially less than 40, 30, 20, 10 or 5 µg, most especially less than 1 µg or 0.5 µg of dsRNA per plant. When the composition is administered to the leaf of the plant, less than 100 µg of dsRNA per leaf may be administered to the plant, especially less than 50 µg, more especially less than 40, 30, 20, 10 or 5 µg, most especially less than 1 µg or 0.5 µg or 0.1 µg of dsRNA per leaf is administered to the plant.

The composition or preparation may include an effective amount of dsRNA. The term "effective amount" means that a sufficient quantity of dsRNA is administered so as to affect the targeted insect.

In a seventh aspect, the present invention provides dsRNA adsorbed onto a molecule having a plurality of positively charged groups. Features of the seventh aspect of the present invention may be as described for the first aspect of the present invention.

In an eighth aspect, the present invention provides a molecule having a plurality of positively charged groups adsorbed onto a clay. Features of the eighth aspect of the present invention may be as described for the first aspect of the present invention.

In a ninth aspect, the present invention provides a method of preparing the preparation of the second aspect of the present invention. This method may include the step of mixing the composition of the first aspect of the present invention with a fluid, such as a liquid, especially an aqueous liquid. The method may also include the step of mixing the composition with one or more other active agents or other agents, as defined in the second aspect of the present invention. Features of the ninth aspect of the present invention may be as described for the second aspect of the present invention.

In a tenth aspect, the present invention provides double-stranded RNA adsorbed onto a clay complex. Features of the tenth aspect of the present invention may be as described for the first aspect of the present invention.

In an eleventh aspect, the present invention provides a kit comprising:
  (i) A clay complex (or a clay and a molecule having a plurality of positively charged groups); and
  (ii) dsRNA;
wherein the dsRNA is adsorbable onto the clay complex.

In one embodiment of this aspect, the clay complex (or the clay and the molecule having a plurality of positively charged groups) and/or the double-stranded RNA is provided in solid or liquid (especially aqueous) form. The clay complex (or the clay and the molecule having a plurality of positively charged groups) and/or the dsRNA may, depending on their form, include a variety of other agents. Exemplary agents include, but are not limited to, one or more of the following types of ingredients: diluents, carriers, excipients, suspension agents, agglomeration agents, bases, buffers, bittering agents, fragrances, preservatives, propellants, surfactants, thixotropic agents, anti-freezing agents, and colouring agents. Suitable agents may be selected by a skilled person.

The kit may also include one or more other active ingredients. An active ingredient, as defined herein, is an ingredient that provides benefit to a plant. The active ingredient may be, for example, an insecticide, a pesticide, a fungicide, an antibiotic, an insect attractant, an anti-parasitic agent, an anti-viral agent, or a nematicide.

Features of the eleventh aspect may be as described for the first aspect of the present invention.

In a twelfth aspect, the present invention provides a composition comprising dsRNA adsorbed onto a clay complex, and wherein the clay complex includes positively charged groups having a pKa of greater than 7.5. Features of the twelfth aspect may be as described above for the first aspect of the present invention.

In a thirteenth aspect, the present invention provides a composition comprising a clay complex and a negatively charged active agent. The negatively charged active agent may be dsRNA or a chemical agent (including insecticides). Features of the thirteenth aspect of the present invention may be as described for the first aspect of the present invention.

In a fourteenth aspect, the present invention provides a method of adversely affecting an insect or insect population, the method comprising the step of administering the composition of the first or thirteenth aspect of the present invention to the insect or insect population. The step of administering the composition may include administering (or applying) the composition to an insect food for consumption by the insect or insect population (or individuals within that population). Features of the fourteenth aspect of the present invention may be as described above for the first aspect of the present invention. The insect food may be as described for the fourth aspect of the present invention.

Any of the features described herein can be combined in any combination with any one or more of the other features described herein within the scope of the invention.

BRIEF DESCRIPTION OF DRAWINGS

Various embodiments of the invention will be described with reference to the following drawings, in which:

FIG. 4A provides a gel electrophoresis image of dsRNA release from a dsRNA-etPEI complex, with an N/P ratio of 3 (i.e. NP3; N: amine in PEI and P: phosphate in dsRNA);

FIG. 4B provides a gel electrophoresis image of dsRNA release from a dsRNA-etPEI complex, with an N/P ratio of 4 (i.e. NP4; N: amine in PEI and P: phosphate in dsRNA);

FIG. 5 illustrates the change in pH of a etPEI solution as increasing volumes of NaOH is added;

FIG. 6A provides a gel electrophoresis image in which the presence of free dsRNA is investigated in a Bentonite-etPEI-dsRNA complex with a N:P ratio of 3 (N: amine in PEI and P: phosphate in dsRNA; denoted BReP3) at pH 8.0 and 8.5;

FIG. 6B provides a gel electrophoresis image in which the presence of free dsRNA is investigated in a Bentonite-etPEI-dsRNA complex with N:P ratios of 4 and 5 (N: amine in PEI and P: phosphate in dsRNA; denoted BReP4 and BReP5) at pH 8.0 and 8.5;

FIG. 10A is a scanning electron microscope image of bentonite;

FIG. 10B is a scanning electron microscope image of BEN-etPEI;

FIG. 11 illustrates the particle size distribution of bentonite, etPEI, etPEI-dsRNA complex, and BEN-etPEI-dsRNA;

FIG. 12 is a gel electrophoresis image illustrating the nuclease protection of dsRNA in BReP5 in a high salt Nuclease A bioassay;

Figure 1A:
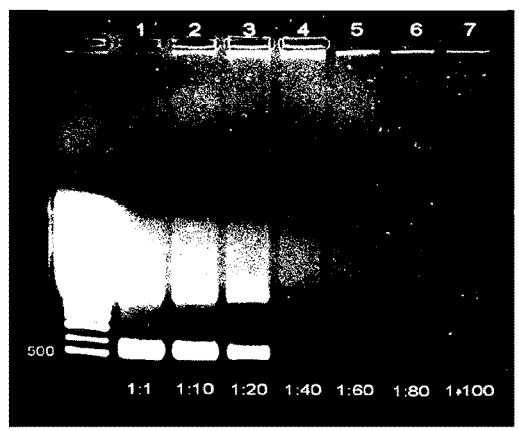
FIG. 1A provides a gel retardation image of bentonite-polyethyleneimine-dsRNA compositions (BEN-PEI-dsRNA) at different dsRNA:BEN-PEI loading ratios, in which the polyethyleneimine (PEI) has a molecular weight of 60,000.

Preferred features, embodiments and variations of the invention may be discerned from the following Examples which provides sufficient information for those skilled in the art to perform the invention. The following Examples are not to be regarded as limiting the scope of the preceding Summary of the Invention in any way.

EXAMPLES

Targets for Topical Application of dsRNA

Targets for the composition of the present invention or dsRNA gene sequences for use in the composition of the present invention include (unless otherwise stated, the sequences below are intended to target *Helicoverpa armigera*):

Rieske gene—The Rieske gene expresses an iron sulphur cluster involved in the electron transport chain (ETC) which when targeted by RNAi causes mortality in insects. The cDNA sequence used for the Rieske gene (which corresponds to the RNA sequence) is provided in SEQ ID NO. 1 below (300 bp):

CGCATACACCAGCTGAAAAGGTGTTGGTGCACCCCTTGCCAAAAACCTCG

ACTGTGGAGTCACTGCATGGATCCCTGCCTATCCAGGGCTTGAAGGCCAG

AGTAAACGGTCGCGTTTTGTTAAATATTTCTGGGGATTTACGACGAAAAA

TCGTGTTACATAACACCTTGTCACTTCTAGGGCCAAGCCATGTACGTTTC

GCGCATACCGACATCAGCTACCCCGACTTCTCGGCGTACCGTCGCAAGGA

GACGCAGGATCCCACCTCAAGGGCTAACGACAACGTCGATGGACGTCAGT

Voltage-Dependent Anionic Channels (VDAC)—VDACs are integral membrane proteins forming pores in the mitochondrial outer membrane. VDACs act as general diffusion pores for small molecules such as ATP, phosphocreatine, and small ions. They have also shown to be involved in apoptotic pathways. The cDNA sequence used for the VDAC gene (which corresponds to the RNA sequence) is provided in SEQ ID NO. 2 below (232 bp):

GCGCTAGACGCCGACGCGTCTCTGCATGCCAAGGTCAACAACAAATCTCT

CATTGGTCTTGGATACCAACAGAAGTTGCGCCCAGGCGTGACTTTGACAA

TTTCTGCTGCTATCGATGGCCAGAACTTCAACGCTGGTGGACACAAAGTG

GGTGTCGCCCTGGAGCTCGAGCCCTAAGTACACAGAGGCGCTTCGGCTTT

TAGTCCTGTAGATAATACATAATGCCACACTG

Green Fluorescent Protein (GFP)—GFP was used as a negative control in some experiments. The cDNA sequence used for GFP (which corresponds to the RNA sequence) is provided in SEQ ID NO. 3 below (339 bp):

AGGACGACGGCAACTACAAGACCCGCGCCGAGGTGAAGTTCGAGGGCGAC

ACCCTGGTGAACCGCATCGAGCTGAAGGGCATCGACTTCAAGGAGGACGG

CAACATCCTGGGGCACAAGCTGGAGTACAACTACAACAGCCACAACGTCT

ATATCATGGCCGACAAGCAGAAGAACGGCATCAAGGTGAACTTCAAGATC

CGCCACAACATCGAGGACGGCAGCGTGCAGCTCGCCGACCACTACCAGCA

GAACACCCCCATCGGCGACGGCCCCGTGCTGCTGCCCGACAACCACTACC

TGAGCACCCAGTCCGCCCTGAGCAAAGACCCCAACGAGA

Control—MEGAscript® RNAi kit control (500 bp).
Arginine Kinase (AK) gene—targeting the AK gene may affect the muscles of an insect.
The AK gene is mainly involved in energy metabolism. The cDNA sequence for the AK gene (which corresponds to the RNA sequence) is provided in SEQ ID NO. 4 below (200 bp):

GATGACAGGCTTGGTTTCCTGACTTTCTGCCCCACCAACTTGGGAACCAC

CGTGCGTGCCTCCGTGCACATCAAGCTGCCCAAGCTGGCTGCCGACAAGG

CCAAGCTGGAGGAGATCGCATCCAAGTACCACCTGCAGGTGCGCGGAACC

CGCGGCGAGCACACCGAGGCTGAGGGCGGCGTCTACGACATCTCCAACAA

Sarco/endoplasmic reticulum Ca$^{2+}$-ATPase (SERCA) gene—targeting the SERCA gene may affect the muscles of an insect. The SERCA gene is involved in calcium uptake in the endoplasmic reticulum. The cDNA sequence for the SERCA gene (which corresponds to the RNA sequence) is provided in SEQ ID NO. 5 below (231 bp):

TTCCTTGAATTCGAAATTACTGGCTCCACCTACGAACCCATTGGTGACGT

TTACCTGAAGGGACAGAAGATCAAGGCCGCTGAATTCGATGCTCTGCACG

AACTTGGTACCATTTGCGTTATGTGCAATGACTCCGCTATTGATTTCAAC

GAATTCAAACAGGCTTTCGAAAAGGTCGGTGAGGCCACTGAAACCGCTCT

TATCGTCCTCGCTGAGAAAATGAACCCCTTC

Glutathione Transferase (GTT) gene—targeting the GTT gene may affect the gut of an insect. The GTT gene is important in the detoxification of compounds. The cDNA sequence for the Glutathione S-transferase gene (which corresponds to the RNA sequence) is provided in SEQ ID NO. 6 below (300 bp):

GAAAGCAGATGAGGCTCTGCTCAAGAAGCTGGAGGAAGCTCTGCACTTCC

TCAACACATTCCTCGAAGGTCAGAAGTACGCTGCGGGTGACAAACTGACC

TTGGCAGACCTCAGTCTCGTGGCGACTGTGTCCACTATAGACGCCGTCGA

CATCAGCCTGAAGGAATATCCCAATGTTGAAAAGTGGTTCGAGCTGGTGA

AAGCGACTGCCCCGGGATACCAGGAAGCAAATGAAGCTGGCCTTAAAGCA

TTCAGAGCTATGGTAGCGCAGTTAAAAGCTAAAACTGAATTGTAAGTGTA

Acetylcholinesterase (AchE) gene—targeting the AchE gene may affect the body wall and appendages of an insect. The AchE gene is important in growth and development. The cDNA sequence for the AchE gene (which corresponds to the RNA sequence) is provided in SEQ ID NO. 7 below (310 bp):

GAGTGGAGACTCAACGAAGATCAATTGGCCGGTGCACACGGCGTCCGGGC

GTGAATACCTGTCCTTAGCAGTCAACTCCAGCTCCATAGGCCACGGGCTG

AGGGTCAAGGAGTGCGCCTTCTGGCAGAAGTACTTGCCACAGTTGATGGC

TGCCACCAATAAGCCAGAACCTCCGAAGAATTGCACGAACAGCGCAGCGC

CCGTCAAGGTCCCGTACGAAATCTTCGGCGTGGGCGTCGTGATAGCTACG

GGCTTAGCCAAGACAACGTGGTTCAAGTACATCATATGAGTTCATTATGT

GGTCTAAGAG

Juvenile hormone esterase gene—The cDNA sequence for the juvenile hormone esterase gene (which corresponds to the RNA sequence) is provided in SEQ ID NO. 8 below (309 bp):

CCACCAAGATCTACACGGACCAGAATATTTGGTCAGCAAGAATGCCATCG

TCATCACATTTAATTACAGATTGAACGTCTTCGGTTTCCTGTCCATGAAT

ACGACAAAAATCCCCGGCAACGCTGGTCTCCGAGACCAGGTGACCCTGTT

GCGCTGGGTGCAGAGAAATGCTAAGCATTTCGGAGGAGACCCCAACAACG

```
TCACCATAGCGGGGCAGAGCGCTGGTGCAGCAGCCGCGCATCTATTGACT

CTGTCTAAAGCTGCTAAAGGTCTTTTCAAAAGAGCAATCTTGATGAGCGG

AACAGGAAT
```

Methoprene-tolerant (Met) receptor gene—the Met receptor is an intracellular receptor in the insect. The cDNA sequence for the Met receptor gene (which corresponds to the RNA sequence) is provided in SEQ ID NO. 9 below (375 bp):

```
GCCGCATAGATGGCATTCTAAGGCGTTCCGATAAAGCCACATCAAATGGT

GTTCAGGATGAGCAAATTATAAGAAGGCAAAGAGTAAGAACTAATAGAAC

ATTTTCATCCAGTGGGAATGATGTTGTTTTTATTGGTATGATTCATGTTC

TATCCAGTGCAATGCCACCTCGAATTCTACCCCCTACAGCCTATTCAGAA

TACTGGACGAGACATTTGATTGATGGTCGTATCGTTCAGTGTGACCAGAG

TATATCATTAGCAATTGGCTACATGACAGAAGAAGTTACTGGAACATCTG

CTTTCGTCTTCATGCACAAAGATGATGTCCGCTGGGTAATTTGTGTATTA

CGACAAATGTATGATGAGAGCCGGG
```

Rab4b GTPase gene—Rab4b GTPase is a GTPase hydrolase enzyme. The cDNA sequence for the Rab4b GTPase gene (which corresponds to the RNA sequence) is provided in SEQ ID NO. 10 below (313 bp):

```
AGGACATGGAGGAATCAAGAGAAGTCACTTTTACAGAAGCTAGTCAATTT

GCCCAAGAAAATGAATTGATGTTTCTTGAAACCAGTGCTAAAACAGGTGA

AAATGTAGAAGAAGCTTTCTTGAAATGTTCCAAAACAATTTTGGCTAAAA

TTGAAACAGGTGAATTAGATCCCGAGCGAATAGGTTCAGGCATTCAATAT

GGGACTGGGACCTCTAAAAGGCTTAGCGCGCCCAAGAAACCTGCAAGAAG

TCCATCTGATTGTGCTTGTCATGTATAACATTATTTCTTGGATACATAGA

ATGCATGATCTGC
```

Prophenoloxidase gene—targeting the prophenoloxidase gene may affect the foregut of an insect. The prophenoloxidase gene is involved in detoxification of compounds. The cDNA sequence for the prophenoloxidase gene (prophenoloxidase subunit 2) (which corresponds to the RNA sequence) is provided in SEQ ID NO. 11 below (242 bp):

```
ACGATTCCGTTCGAACAGACGTTCCGTGACCTCTCTGTTCAGAGCAACGA

CCCTCGCCGCCCCAACTTGGCCGAGTTCAACTTCTGCGGTTGCGGCTGGC

CCCAGCACATGTTGGTCCCCAAGGGTACTGAGGCGGGCGCCGCCTACCAG

TTGTTCGTTATGCTTTCGAACTACGATCTTGACAGCGTGGAACAACCTGA

CGGCTCACAGTTGAGCTGCGTCGAAGCTTCCAGTTTCTGCGG
```

Cathepsin L gene—targeting the cathepsin L gene may affect the cuticle and epidermis of an insect. The cathepsin L gene plays an important role in the moulting process. The cDNA sequence for the cathepsin L gene (which corresponds to the RNA sequence) is provided in SEQ ID NO. 12 below (280 bp):

```
GGTGGAGGACAAGTTCCGCATGAAGATCTACCTGGAGAACAAGCACCGCA

TCGCCAAGCACAACCAGCGCTTCGAGCAGGGCGCCGTCAGCTACAAGCTG

CGCCCCAACAAGTACGCCGACATGCTCAGCCACGAGTTCGTGCACGTCAT

GAACGGCTTCAACAAGACCCTCAAGCACCCGAAGGCCGTGCACGGCAAGG

GTCGCGAGTCCCGGCCCGCCACGTTCATCGCGCCGGCGCACGTCACCTAC

CCCGACCACGTGGACTGGCGCAAGAAGGGC
```

NV2 gene—targeting the NV2 gene may affect the mitochondria of an insect. The NV2 gene plays an important role in the electron transport chain (ETC). The cDNA sequence for the NV2-1 gene (which corresponds to the RNA sequence) is provided in SEQ ID NO. 13 (374 bp) below:

```
GCCACAAGCGTGGTGCCATGATCCCACTGCTCGACCTGGCTCAGCGTCAG

GCTGGAGGTTGGCTGCCGATATCTGCCATGCATAAAGTAGCTGAAATCCT

CAAACTTCCTCGCATGAGAGTTTATGAGGTTGCTACGTTCTACACTATGT

TTATTAGACGACCAATCGGCAAGTACCATATCCAAGTTTGCACGACAACT

CCTTGCTGGCTCCGAGGTTCTGATGCTATCCTGAAAGCTCTCACTGAGGG

TACACAATGCCATGTTGGAGGAAACAGCCCTTGTGGCAAGTTCTCTATTT

CTGAGGTTGAATGCCTTGGTGCCTGTGTTAATGCTCCTATGATTCAAGTC

AACGATGATTACTACGAAGACCTG
```

The cDNA sequence for the NV2-2 gene (which corresponds to the RNA sequence) is provided in SEQ ID NO. 14 (255 bp) below:

```
GGTTGAATGCCTTGGTGCCTGTGTTAATGCTCCTATGATTCAAGTCAACG

ATGATTACTACGAAGACCTGTCAGTAGATGACACAAAGGAAATTATTGAA

AAGCTCAAAAGGGACGAGAAACCGAAAGCTGGCCCTAGGAGCGGCAGATT

CGCCTCAGAACCCTTGGGAGGACTCACTTCTCTCACCGAAGAACCTACAG

GCCCCGGTTTTGGACTACAACCCGGCCTCAAGGCCTAGAACAAAAGTTT

CCGTT
```

The experiments below detail the use of the Rieske gene, the VDAC gene, GFP and the Control (MEGAscript®) in the composition. However, it is expected that any of the above sequences may be used for the composition.

Preparation of Double Stranded RNA (dsRNA)

The Rieske gene sequence was cloned into pGEM-T-Easy vector, sequenced and used for in vitro dsRNA synthesis. The T7 promoter sequences were added to gene specific primers (provided below). The T7 DNA template (300 bp) for dsRNA synthesis was synthesised using PCR. The dsRNA synthesis was performed using MEGAscript T7 Transcription Kit and purified by Trizol extraction protocol. The dsRNA concentration was analysed using NanoDrop 1000 and integrity was checked by agarose gel electrophoresis (1%). The primer sequences used were as follows (T7 sequence underlined):

SEQ ID NO. 15:
TAATACGACTCACTATAGGGAGTCGGGGTAGCTGATGTCG

SEQ ID NO. 16:
TAATACGACTCACTATAGGGAGGCAAGTTCATCGGTGGTT

The Rieske and VDAC sequences were also synthesised by an in vitro transcription method by AgroRNA company (Seoul, South Korea). The Rieske sequence is 300 bp (conserved region of sequence) and the VDAC sequence is 232 bp (conserved region of sequence), as outlined above.

Example 1—Bentonite-Polyethyleneimine-dsRNA (BEN-PEI-dsRNA) Composition

In general, bentonite-polyethyleneimine (BEN-PEI) was prepared first by mixing dispersed bentonite in excess PEI solution overnight (~16 hrs) followed by washing away of excess PEI and dispersing the collected BEN-PEI. dsRNA was mixed with the dispersed BEN-PEI at varied dsRNA: BEN-PEI mass ratios, which was subjected to the gel test to determine the best loading ratio of dsRNA and BEN-PEI. Polyethyleneimine (PEI) was purchased from Sigma Aldrich, and had a molecular weight of 60,000 and 800.
Preparation of BEN-PEI BEN-PEI was prepared, using PEI with both a molecular weight of 60,000 and a molecular weight of 800. First, 1 g of bentonite (supposed Cation Exchange Capacity (CEC) was 100 meq/100 g) was dispersed in 20 mL deionised water by stirring overnight. Next, 0.5 g of a 50% PEI solution (molecular weight of 60,000 or 800) was dispersed in 10 mL deionized water and the pH was adjusted to 6-7 using 1.0 M HCl while stirring. While vigorously stirring, the dispersed PEI solution was then added dropwise into the bentonite solution. The bentonite PEI solution was stirred overnight at 50° C.

The bentonite-polyethyleneimine (BEN-PEI) complex was then collected and washed five times using high-speed centrifugation (10000 g, 5 min; 20000 g, 10 min; 20000 g, 15 min; 20000 g, 15 min; 20000 g, 15 min). The washed BEN-PEI complex was dispersed in 100 mL deionised water.

The mass concentration was 11.7 mg/ml for BEN-PEI (60,000 molecular weight) and 8.3 mg/ml for BEN-PEI (800 molecular weight). Mass concentration was determined by centrifugation (4,000 rpm, 20 min) of 10 mL sonicated bentonite or bentonite-PEI (BEN-PEI) suspension. Resulting supernatant was discarded and the pellet vacuum-dried (2 hrs), followed by air-drying (16 hrs). The dried pellet was weighed for calculation of the mass concentration.
dsRNA Loading onto BEN-PEI The mass loading ratio, i.e. the ratio of complete dsRNA binding with Ben-PEI was determined by mixing 500 ng MEGAscript control dsRNA (500 bp) with BEN-PEI (60, 000 and 800 molecular weight) at mass ratios of 1:1, 1:10, and 1:20 up to 1:140 and 1:150. The resulting mixtures were subjected to orbital shaking (20 min) followed by gel electrophoresis (1.0%).

Figure 1B:
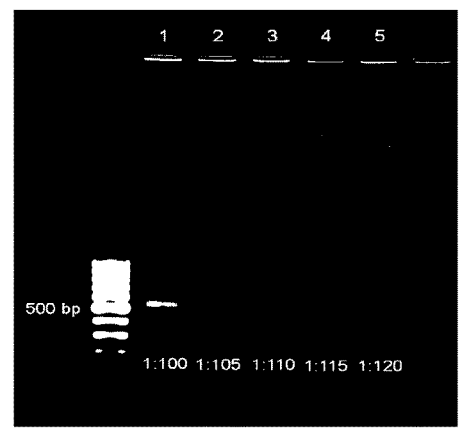
FIG. 1B provides a gel retardation image of bentonite-polyethyleneimine-dsRNA compositions (BEN-PEI-dsRNA) at different dsRNA:BEN-PEI loading ratios, in which the polyethyleneimine (PEI) has a molecular weight of 800.

As illustrated in FIGS. 1A and 1B, as the amount of BEN-PEI relative to dsRNA increased (i.e. the mass ratio from 1:1 to 1:100), the intensity of the bottom band for free dsRNA became weaker in intensity, indicating the formation of more BEN-PEI-dsRNA complexes. Complete binding of dsRNA with BEN-PEI was shown to be around ~1:80 (FIG. 1A, PEI MW 60,000) and ~1:115 (FIG. 1B, PEI MW 800). At these ratios, all dsRNA was associated with Ben-PEI, leaving no free dsRNA to migrate down the gel. This illustrates that BEN-PEI is able to completely load dsRNA at a dsRNA:BEN-PEI mass ratio of 1:80-1:115, depending on the molecular weight of PEI; thus the dsRNA loading capacity is about 1 wt % in the solid system.
pH Dependent Release of dsRNA from BEN-PEI-dsRNA Compositions pH release testing was performed by preparing BEN-PEI-dsRNA solutions at the mass ratio with complete dsRNA association (as discussed in the preceding paragraph: 1:100 for BEN-PEI-dsRNA (in which PEI has a molecular weight of 60,000) and 1:120 for BEN-PEI-dsRNA (in which PEI has a molecular weight of 800)). The resulting suspensions were centrifuged at 13,000 rpm for 15 min and the supernatant electrophoresed (1.0%) to check for the absence of free dsRNA before discarding the supernatant. The pellets were resuspended in 20 µL aqueous solutions ranging from pH 2-12.5, and orbital shaken for 30 min. Gel electrophoresis (1.0%) was then used to examine the release of dsRNA from the BEN-PEI-dsRNA composition, and the results are provided in FIG. 2.

Figure 2A:
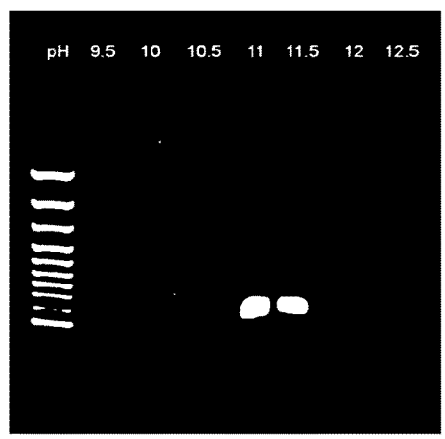
FIG. 2A provides a gel retardation image of dsRNA release from bentonite-polyethyleneimine-dsRNA compositions (BEN-PEI-dsRNA) at various pH, in which the polyethyleneimine (PEI) has a molecular weight of 60,000.
Figure 2B:
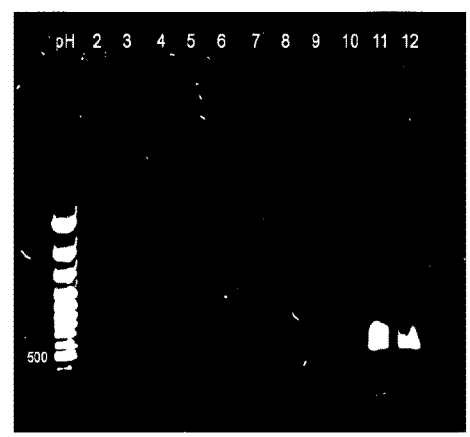
FIG. 2B provides a gel retardation image of dsRNA release from bentonite-polyethyleneimine-dsRNA compositions (BEN-PEI-dsRNA) at various pH, in which the polyethyleneimine (PEI) has a molecular weight of 800.

As illustrated in FIGS. 2A and 2B, the dsRNA release was pH dependent and was substantially released from the compositions at pH 11. However, the pH in the final mixed solution would be lower than the initial value. This means that dsRNA release would start at a pH lower than 11.0 but higher than 10.5.

Example 2—Bentonite-Ethoxylated Polyethyleneimine-dsRNA (BEN-etPEI-dsRNA or BReP) Composition A different polymer was used in the composition instead of PEI: 80% ethoxylated branched polyethyleneimine (et-PEI). This polymer has a molecular weight of 70,000 and is available from Sigma Aldrich.
Preparation of dsRNA-etPEI First, 35% w/w (density=1.05 g/mL) of 80%-ethoxylated branched PEI (etPEI) solution was diluted 1,000 times with deionised water and the pH was adjusted to 7-7.5 using 1.0 M HCl while stirring. The mass concentration of etPEI was then adjusted to 0.35 mg/mL.

Rieske dsRNA (500 ng, insect specific gene, 300 bp, 1.1 µg/uL) was added to etPEI solutions with N:P ratios (N: amine in PEI and P: phosphate in dsRNA) of 1, 2, 3, 4, 5, 10 and 20 (denoted NP1, NP2, NP3, NP4, NP5, NP10 and NP20 herein). The mixtures were then incubated on ice for 15 minutes with gradual mixing by inversion. Gel electrophoresis was used to examine if there is free dsRNA in the dsRNA-etPEI mixed solutions, and these results are provided in FIG. 3.

Figure 3:
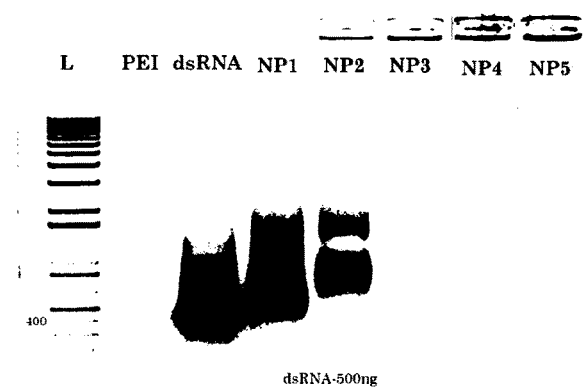
FIG. 3 provides a gel electrophoresis image of dsRNA-etPEI complexes with N:P ratios of 1, 2, 3, 4 and 5 (N: amine in PEI and P: phosphate in dsRNA)

The image provided in FIG. 3 confirmed that some free dsRNA was present in the NP2 (dsRNA-etPEI) solution and a very minimal amount of free dsRNA was present in the NP3 (dsRNA-etPEI) solution. Complete binding of dsRNA with etPEI occurred in the NP4 and NP5 solutions. For the N:P molar ratio of 3, 4, and 5, the dsRNA/etPEI mass ratio was nearly 1.41, 1.05, and 0.84, respectively.
pH Dependent Release of dsRNA from dsRNA-etPEI NP3 and NP4 (dsRNA-etPEI) solutions were prepared, and then mixed in the same volume of buffer. The buffer solutions had a pH of from 8.0 to 10.5. The mixtures were shaken for 30 minutes, and then gel electrophoresis was used to examine the release of dsRNA from the dsRNA-etPEI complexes. The results are provided in FIGS. 4A (for NP3) and 4B (for NP4).

As shown in FIGS. 4A and 4B, there was some free dsRNA in NP3 complexes while almost no free dsRNA in NP4. Both NP3 and NP4 dsRNA-etPEI complexes released a substantial amount of loaded dsRNA at pH 9.5 and 10. NP3 dsRNA-etPEI complexes started to release dsRNA at probably pH 8.5-9.0 while NP4 dsRNA-etPEI complexes started to release dsRNA at pH 9.5. This experiment illustrates that dsRNA release started at pH 9.0-9.5, and that a substantial amount of dsRNA was released at pH 9.5-10 and most released at pH 10.5.

pKa of etPEI

The pKa of 80% ethoxylated branched polyethyleneimine (etPEI) was determined. First, solutions of 0.1 mol/L HCl, etPEI, and NaOH were prepared. 10 mL 0.1 mol/L HCl and 10 mL 0.1 mol/L etPEI were mixed, and the pH recorded. To the etPEI solution was added 0.5 mL 0.1 mol/L NaOH while stirring and the pH recorded; this step was repeated until the pH began to increase sharply. To the etPEI solution was added 0.1 mL 0.1 mol/L NaOH while stirring and the record pH recorded; this step was repeated until the pH increase slowed down. The previous two steps were then repeated until the pH of the solution was 11-11.5. The results are provided in FIG. 5. This illustrates that etPEI has a pKa of about 9.0-9.5.

Preparation of BEN-etPEI-dsRNA (BReP) Composition

The prepared dsRNA-etPEI samples were immobilised with bentonite (BEN) at different BEN:etPEI mass ratios, and then the dsRNA release from the BEN-dsRNA-etPEI (BReP) at different pH values was examined.

Preparation of BReP

First, bentonite (0.5 g) was dispersed in 100 mL deionised water via stirring for 5 minutes, and this suspension was then diluted to a final mass concentration of 5 μg/μL. Next, dsRNA-etPEI mixtures at a N:P ratio of 3, 4 and 5 (i.e. NP3, NP4 and NP5) were prepared as described above.

The bentonite suspension was mixed with the dsRNA-etPEI mixtures (NP3, NP4 and NP5) at a bentonite:etPEI mass ratio of 6:1 to form BEN-etPEI-dsRNA complexes (at NP3, NP4 and NP5—i.e. BReP3, BReP4 and BReP5). The mixtures were incubated on ice for 15 minutes with gradual mixing by inversion and then gel electrophoresis was used to examine for the presence of free dsRNA.

As illustrated in FIGS. 6A and 6B, at pH 8.0-8.5 BReP3 released some dsRNA (FIG. 6A), BReP4 released a little amount of dsRNA (FIG. 6B) and BReP5 released almost no dsRNA (FIG. 6B). In comparison with the gel images in FIGS. 3, 4A and 4B, there is much more free dsRNA in BReP3 and BReP4 than in NP3 and NP4. Without wishing to be bound by theory, it is believed that this is because bentonite sheets carry negative charges which can neutralise some positive charges in etPEI, and neutralisation of positive charges in etPEI can result in release of dsRNA. This effect is expected to decrease at higher N:P ratios in etPEI-dsRNA (such as NP5), and for BReP5 it appears that there are enough positive charges in etPEI to ameliorate this effect.

pH Dependent Release of dsRNA from BReP

BReP4 and BReP5 suspensions were prepared, as described above. The suspensions were then mixed with the same volume of buffer. The buffer solutions had a pH from 8.5 to 10.0. The mixtures were shaken for 30 minutes, and then gel electrophoresis was used to examine the release of dsRNA from the BReP4 and BReP5 complexes. The results are provided in FIGS. 6 and 7.

Figure 7:
FIG. 7 provides a gel electrophoresis image showing the pH dependent release profile of dsRNA from BReP4.

As shown in FIG. 7, a small amount of free dsRNA was present in the BReP4 complex and in dsRNA-etPEI (NP4). The pH dependant release of dsRNA from BReP4 seemed to start at pH 8.5, consistent with that shown in FIG. 6B. The release became more significant at pH 9.0 and 9.5, with the majority of the dsRNA released at pH 10.0.

Figure 8:
FIG. 8 provides a gel electrophoresis image showing the pH dependent release profile of dsRNA from BReP5.

As shown in FIG. 8, the amount of free dsRNA present in the BReP5 and dsRNA-etPEI (NP5) was minimal. The near total release of dsRNA from BReP5 occurred abruptly at pH 9.5, with an almost complete release at pH 10.0.

Figure 9:
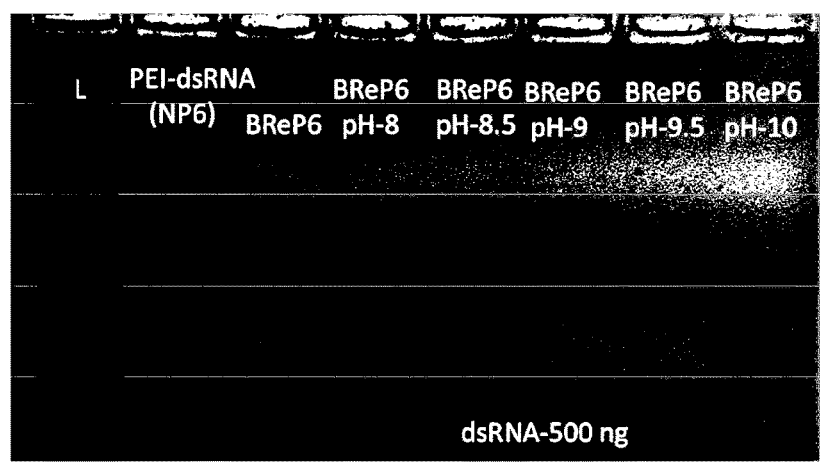
FIG. 9 provides a gel electrophoresis image showing the pH dependent release profile of dsRNA from BReP6.

BReP6 was also prepared to test the pH dependent release behaviour. BReP6 was as prepared above for BReP4 and BReP5, except that the N:P ratio (N: amine in etPEI and P: phosphate in dsRNA) in the etPEI-dsRNA was 6 (i.e. NP6). As shown in FIG. 9, no amount of free dsRNA was observed in the BReP6 and in dsRNA-etPEI (NP6) preparations. The minimal release of dsRNA from BReP6 started at pH 10.0.

Summary

BReP4, BReP5 and BReP6 were able to carry a large amount of dsRNA. For example, the mass ratio BEN:dsRNA:etPEI was 6:1.41:1, 6:1.05:1, 6:0.84:1, and 6:0.70:1 for BReP3, BReP4, BReP5 and BReP6, respectively. This means that the dsRNA wt % was 16.7%, 13.0%, 10.7% and 9% in BReP4, BReP5, and BReP6, respectively.

dsRNA in BReP5 and BReP6 were almost completely associated with BEN-etPEI to form BEN-dsRNA-etPEI complexes, which were stable at pH 6-9, without any obvious release of loaded dsRNA. dsRNA started to release at pH 9.5 and 10.0, for BReP5 and BReP6, respectively. There was a small amount of free dsRNA in BReP4 at pH 7.0-8.5. For BReP4, the release of dsRNA started at pH 8.5-9.0, and completed at pH 10.0.

Physicochemical Properties

Scanning Electron Microscope (SEM) images were recorded in a JEOL JSM-6300 (JEOL, Tokyo, Japan) to investigate the morphology and particle size of bentonite and bentonite-etPEI samples (prepared analogously to the bentonite-PEI samples discussed above). All samples were dropped on silica wafers to avoid immersion into carbon film during coating. As illustrated in FIGS. 10A (for bentonite) and 10B (for BEN-etPEI), BEN-etPEI forms large stacked aggregate (which is negative for the on-leaf residence).

The particle size distribution and zeta potential of bentonite, BEN-etPEI-dsRNA (NP5, as described above), etPEI and etPEI-dsRNA (NP5) were measured on a Nanosizer Nano ZS instrument (Malvern Instruments). FIG. 11 shows the particle size distribution of bentonite, etPEI, etPEI-dsRNA complex, and BEN-etPEI-dsRNA and the z-average value of the particle sizes are ~450, ~7.4, ~750 and ~2110 nm, respectively. The zeta potentials of bentonite, BEN-etPEI complex, etPEI (pH adjusted to ~7), etPEI-dsRNA, and BEN-etPEI-dsRNA were measured and were −32, −25, 18, 0.5, and 1.3 mV, respectively.

Example 3—Nuclease Protection Assay

Rieske dsRNA (500 ng) was loaded on etPEI at a N:P ratios (N: amine in PEI and P: phosphate in dsRNA) of 5 (NP5), as mentioned above. NP5 complexes were then loaded on bentonite at mass ratio of 1:6 to make BReP5. The final volume of the mixture was adjusted to 10 μl using diethylpyrocarbonate (DEPC) water. High salt Nuclease A (2 μl) was added and the mixture incubated at 37° C. for 20 minutes. A buffer at pH 10 (8 μl) was added to release and check dsRNA release from BReP5 complexes. Solutions were loaded on agarose gel (1%) and the gel image recorded. As shown in FIG. 12, naked dsRNA was degraded in the presence of Nuclease A. In sharp contrast, dsRNA in BReP5 was protected from the degradation by Nuclease A, and released at pH 10.

Example 4—Insect Feeding Assay Using BReP5

Insect Rearing

Neonates of *Helicoverpa armigera* were fed on artificial diet for 4 days and were subsequently used in leaf feeding assay. The larvae were reared under controlled conditions of 27±2° C., 65±5% relative humidity and 16:8 h of light and dark cycle.

Leaf Feeding Assay

*Nicotiana tabacum* (1 month old plant) leaves were selected for the insect feeding assay. The assay included four groups of randomly apportioned insects and leaves, with 8 replicates for each group. The groups were: DEPC water (negative control), BEN-etPEI, naked Rieske dsRNA and BReP5.

To perform the assay, the single tender leaf was placed on a moist filter paper in a petri-plate. A composition was spread on both sides of each leaf using a paint brush. The compositions used were: naked dsRNA: 50 μg/100 μL DEPC water; BReP5: corresponding to 50 μg dsRNA/100 μL; BEN-etPEI: at 6:1 bentonite:etPEI—the same mass as of BReP5 in 100 μL; or water: 100 μL. Four day old larvae were transferred to petri-plates and fed with the first fresh leaves with respective treatments for three days, and then repeated with second fresh leaves treated similarly for another three days. After the sixth day of treatment feeding, larvae were shifted to standard artificial diet for further growth.

Figure 13:
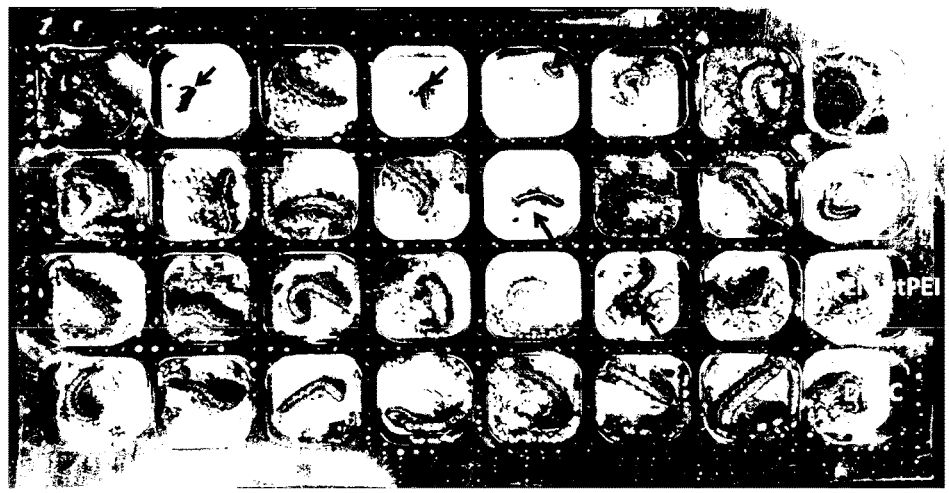
FIG. 13 is a photograph illustrating the mortality of H. armigera fed with DEPC water, BEN-etPEI, naked Rieske dsRNA and BReP5. Dead larvae was indicated by red arrows.
Figure 14:
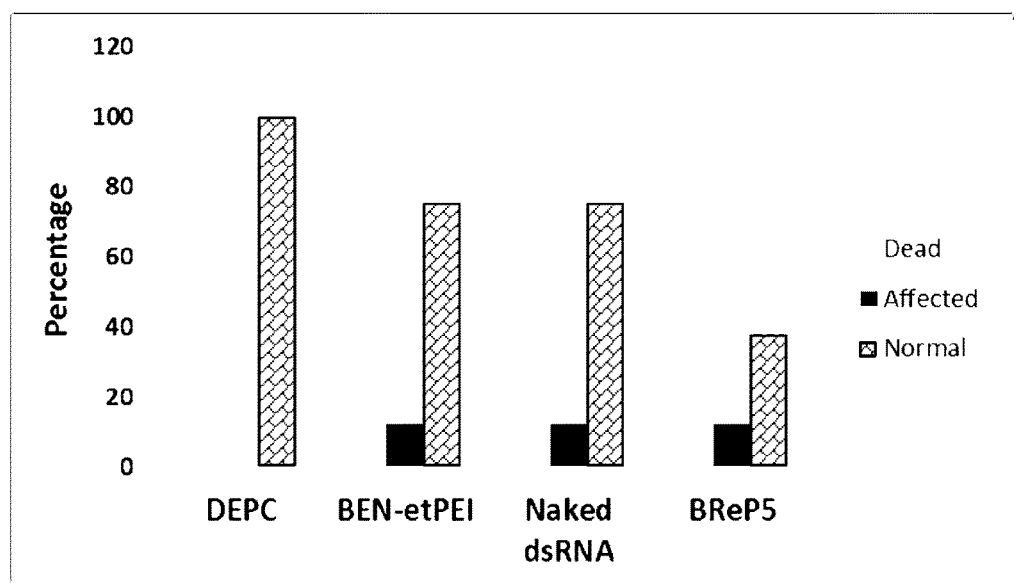
FIG. 14 provides statistical data for the effect at day 12 of ingestion by larvae of Nicotiana tabacum leaves coated with DEPC water, BEN-etPEI, naked Rieske dsRNA and BReP5.

As illustrated in FIG. 13, no mortality was observed in DEPC water only treated group. In the group treated with BEN-etPEI only, one larva was dead and one larva was obviously affected in growth. Comparatively, naked dsRNA treatment group showed a single mortality. In contrast, BReP5 treatment showed mortality in four larvae with one larvae also showing retarded growth. The statistical data are also presented in FIG. 14 and shows the mortality rate in BReP5-treated group is obviously higher than in other groups.

Example 5—Bentonite-pDMAEMA-dsRNA (BEN-pDMAEMA-dsRNA) Composition pDMAEMA pDMAEMA is poly(2-dimethylaminoethyl methacrylate), of the structure shown below. pDMAEMA is a pH-sensitive polymer with a pKa of 7.0-7.5. pDMAEMA can be readily synthesised by reversible addition fragmentation chain transfer (RAFT) radical polymerization with a predetermined molecular weight and narrow molecular weight distribution. In one embodiment, pDMAEMA has an average molecular weight of 15,000 Dalton. However, in this example the pDMAEMA has a molecular weight of 33,000. pDMAEMA may be prepared according to the method outlined in Fournier D et al., (2007) Macromolecules, 40, 915-920.

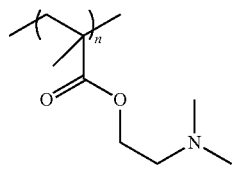

Preparation of dsRNA pDMAEMA pDMAEMA powder was dissolved in deionised water and the pH was adjusted to 6-6.5 using 1.0 M HCl while stirring. The mass concentration of pDMAEMA was then adjusted to 4 mg/mL.

Control dsRNA (500 ng, MEGAscript RNAi kit, 1 μg/μL) was added to pDMAEMA solutions with N:P ratios (N: amine in pDMAEMA and P: phosphate in dsRNA) of 0.5, 1, 2, and 3 (denoted NP1/2, NP1, NP2, and NP3 herein). The mixture was incubated at room temperature (RT) for 5 minutes with gradual mixing by inversion. Gel electrophoresis was used to examine if there is free dsRNA in the dsRNA-pDMAEMA solutions, and results are provided in FIG. 15.

Figure 15:
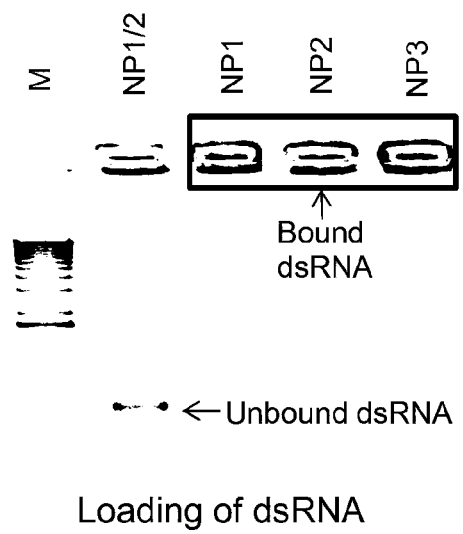
FIG. 15 provides a gel electrophoresis image of dsRNA-pDMAEMA complexes with N:P ratios of 1/2, 1, 2, and 3 (N: amine in pDMAEMA and P: phosphate in dsRNA), in which pDMAEMA has molecular weight of 33,000.

The image provided in FIG. 15 confirms that some free dsRNA was present in the NP1/2 (dsRNA-pDMAEMA) solution. Complete binding of dsRNA with pDMAEMA occurred in the NP1, NP2 and NP3 solutions.

An N:P ratio of 1 means that the mass ratio of pDMAEMA:dsRNA is about 1:2. This is because the molecular weight of the monomeric unit in pDMAEMA is 157 (and this unit has only one nitrogen atom), and the average molecular weight of a single base-sugar-phosphate unit in DNA is about 330 (this unit includes one phosphorous atom). Ben-pDMAEMA-dsRNA may have approximately 63 wt % of Ben, 13 wt % of pDMAEMA and 25 wt % of dsRNA.

Preparation of dsRNA-pDMAEMA-BEN

Bentonite (0.5 g) was dispersed in 80 mL deionised water via stirring for 5 minutes, and this suspension was then diluted to a final mass concentration of 5 μg/μL. The dsRNA was added into the pDMAEMA solution at pH 6.0 to make dsRNA-pDMAEMA mixtures at the N:P ratio of 1 (NP1). The bentonite suspension was then mixed with the dsRNA-pDMAEMA mixtures (NP1) at a bentonite:pDMAEMA mass ratio of 5:1 to form a BEN-pDMAEMA-dsRNA complexes (at NP1—i.e. BPR5). The mixtures were incubated on ice for 15 minutes with gradual mixing by inversion.

pH Dependent Release of dsRNA from dsRNA-pDMAEMA-BEN

A series of buffer solutions of BPR5 (as prepared above) were prepared at pH 8, 8.5, 9, 9.5, 10, 10.5 and 11. Each of the solutions was prepared with same volume buffer. The mixture was incubated at room temperature (RT) for 5 minutes with gradual mixing by inversion, and then gel electrophoresis was run to examine the release of dsRNA from the dsRNA-pDMAEMA-bentonite complexes. The result is provided in FIG. 16.

Figure 16:
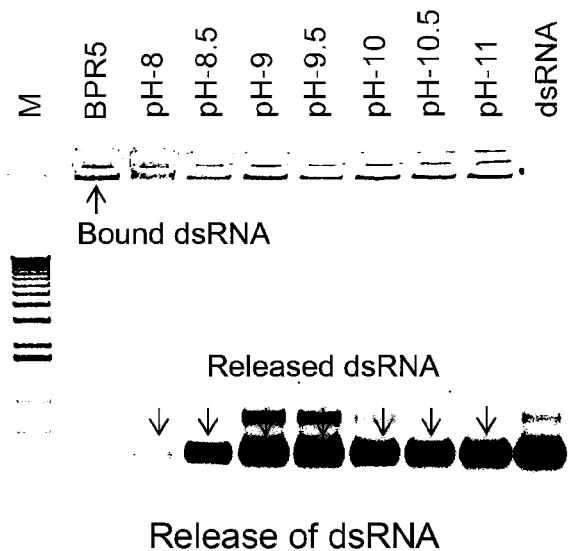
FIG. 16 provides a gel retardation image of dsRNA release from bentonite-pDMAEMA-dsRNA (BPR) complex with an N/P ratio of 1 (i.e. NP1, N: amine in pDMAEMA and P: phosphate in dsRNA) and a mass ratio of bentonite:pDMAEMA of 5:1 (i.e. BPR5), in which pDMAEMA has molecular weight of 33,000.

As shown in FIG. 16, NP1 dsRNA-pDMAEMA-bentonite complexes started to release dsRNA probably at pH 8.0, and that a substantial amount of dsRNA was released at a pH of from 8.5-11.

Example 6—Nuclease Protection Assay

Figure 17:
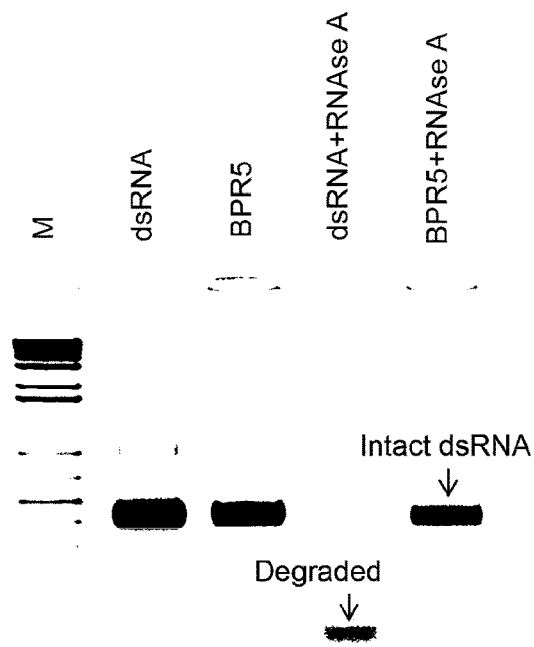
FIG. 17 is a gel electrophoresis image illustrating the nuclease protection of dsRNA in BPR5 in a low salt Nuclease A bioassay.

Control dsRNA (500 ng) was loaded on pDMAEMA at an N:P ratio (N: amine in pDMAEMA and P: phosphate in dsRNA) of 1 (NP1), as mentioned above. NP1 complexes were then loaded on bentonite at a mass ratio of 1:5 to make BPR5. The final volume of the mixture was adjusted to 10 μL using diethylpyrocarbonate (DEPC) water. High salt Nuclease A (0.125 ng) was added and the mixture incubated at 37° C. for 20 minutes. A buffer at pH 10 (8 μl) was added to release and check dsRNA release from BPR5 complexes. Solutions were loaded on agarose gel (1%) and the gel image recorded. As shown in FIG. 17, naked dsRNA was degraded in the presence of Nuclease A. In sharp contrast, dsRNA in BPR5 was protected from the degradation by Nuclease A, and released at pH 10.

Example 7—Feeding Bio-Assay

Newly emerged neonates of Helicoverpa armigera were fed on water, bentonite-pDMAEMA (bentonite polymer or BP), Green Fluorescent Protein (GFP—negative control), Rieske, VDAC, bentonite-pDMAEMA-Rieske (BP-Rieske) and bentonite-pDMAEMA-VDAC (BP-VDAC). BP-Rieske and BP-VDAC were prepared as outlined above for dsRNA-pDMAEMA-BEN, with a N:P ratio of 1 (nitrogen in pDMAEMA:phosphorous in dsRNA), and a mass ratio of bentonite:pDMAEMA of 5:1. Solutions were applied onto the surface of artificial diet cubes (~1 cm$^2$) such that 60 µg dsRNA was applied to each cube (a volume of 100 µL), and the solutions were allowed to percolate into the diet cubes. The resultant cubes were subsequently fed to newly emerged neonates of Helicoverpa armigera. Solutions were fed to the larvae three times with an interval of 24 hours between consecutive feeding. New artificial diet cubes were used at the time of application of the dsRNA solutions.

During the feeding experiment, 15 larvae from each of the treatment groups were pooled together in liquid nitrogen 3 days after their first dsRNA exposure (DPE). The gene silencing effects were analyzed in terms of relative transcripts.

RT-PCR Analysis

To evaluate the effectiveness of the nanoparticle-based RNAi method in silencing both Rieske and VDAC genes through H. armigera larval feeding, dsRNAs for Rieske (300 bp—conserved region of sequence) and VDAC (232 bp—conserved region of sequence) were synthesized through AgroRNA company (Seoul, South Korea).

Total RNA was extracted from 15 pooled larvae and TriSure reagent (Bioline) and DNAse (Thermo Fisher) treatments were performed as per the manufacturer's instructions. Real time reaction was carried out in 204 using 100 ng of total RNA. A gene encoding ribosomal protein (L27, RPL27) was used as an internal reference. Real time PCT (RT-PCR) was performed with a sensifast SYBR No-ROX one step kit (Bioline), and the $2^{-\Delta\Delta C_T}$ method was used to evaluate the transcript levels of Rieske and VDAC relative to GFP in the H. armigera fed on the artificial diets. Primer pairs without overlapping with dsRNA regions were synthesized for examining the suppression of gene transcript by quantitative real-time PCR. The sequences of primers used were as follows.

SEQ ID NO. 17 (Rieske):
CCGCAAACGAGATTAGCACC

SEQ ID NO. 18 (Rieske):
ACTTCGGCGGCTACTACTG

SEQ ID NO. 19 (VDAC):
GACTGCGGTATTAGCATGAAG

SEQ ID NO. 20 (VDAC):
CAGAGAACACTTGAAGATACTG

SEQ ID NO. 21 (RPL27):
ACAGGTATCCCCGCAAAGTGC

SEQ ID NO. 22 (RPLS27):
GTCCTTGGCGCTGAACTTCTC

Figure 18:
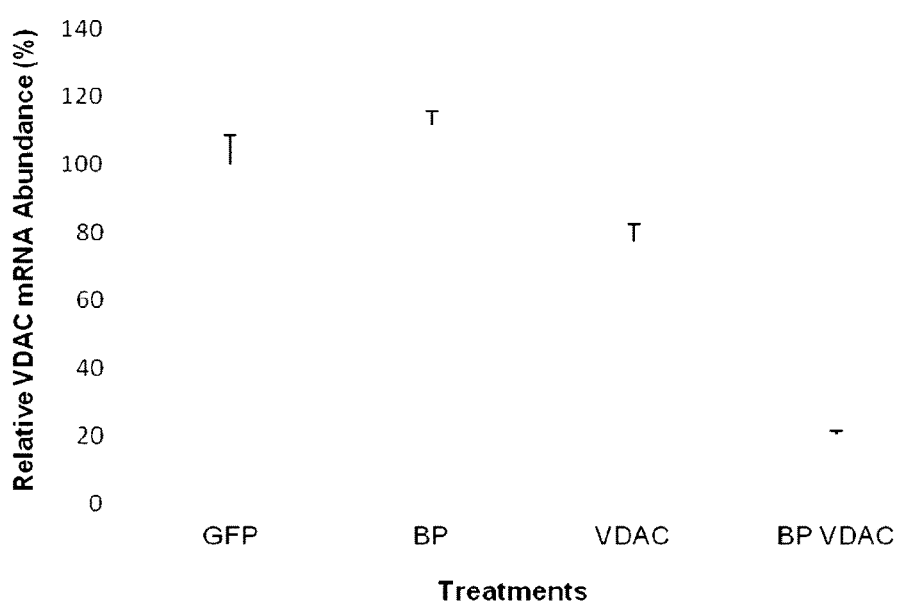
FIG. 18 is a graph of relative transcript levels of VDAC in *Helicoverpa armigera* larvae continuously fed for 3 days (once a day) on GFP dsRNA (as control), bentonite-pDMAEMA (BP), VDAC dsRNA, and bentonite-pDMAEMA-VDAC (BP VDAC). The data are presented as means±SD.
Figure 19:
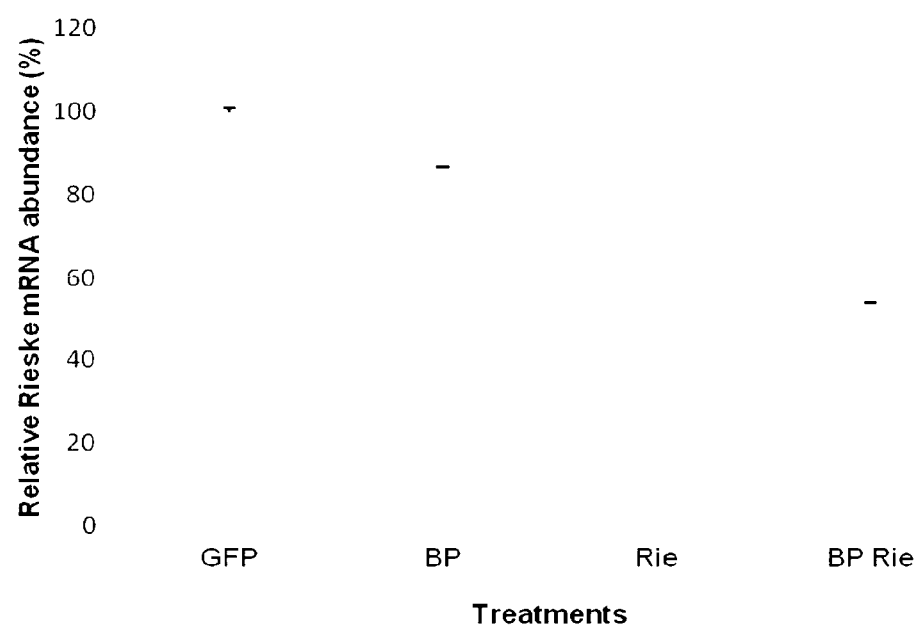
FIG. 19 is a graph of relative transcript levels of Rieske in *Helicoverpa armigera* larvae continuously fed for 3 days (once a day) on GFP dsRNA (as control), bentonite-pDMAEMA (BP), Rieske dsRNA and bentonite-pDMAEMA-Rieske (BP Rie). The data are presented as means±SD.

FIGS. 18 and 19 show that feeding H. armigera larvae with either bentonite-pDMAEMA-Rieske (BP-Rieske) or bentonite-pDMAEMA-VDAC (BP-VDAC) effectively triggered RNAi in the larvae. The BP-Rieske and BP-VDAC repressed the transcript level by 42.8% and 79.4% respectively compared to GFP dsRNA fed larvae. However, naked VDAC dsRNA repressed the transcript level by 22.6% and naked Rieske dsRNA did not suppress the transcript level significantly.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

Advantages

Advantages of the present invention may include:

dsRNA of a large size can be included in the composition;

the dsRNA in the composition may be protected from nucleases and U.V. light;

the molecule having a plurality of positively charged groups may act as a 'pH control' switch to release the dsRNA from the composition at an alkaline pH (for example, for Lepidopteran insects this occurs in the midgut);

after being sprayed on an insect food, the dsRNA should be viable for weeks;

the composition has the capacity to cause mortality of insects feeding on food sources sprayed with or comprising the composition;

dsRNA is highly specific to a target organism and is ecologically friendly. The composition should not affect species that are not targeted by the composition;

the composition may be prepared easily at relatively low cost;

the composition may have a high dsRNA loading capacity;

the composition may have a low toxicity; and the composition may be readily dispersed for spraying, drip-feeding or application via irrigation.

The invention claimed is:

1. A composition comprising double stranded RNA adsorbed onto a clay complex,
    wherein the clay complex comprises:
        a cationic clay; and
        a molecule comprising a plurality of positively charged groups, said positively charged groups being positively charged in a solution having a pH from 5.0 to 7.0, and said positively charged groups having a pKa of greater than 7.0;
    wherein the composition comprises from 0.5 wt % to 40 wt % double stranded RNA, and
    wherein the mass ratio of clay to molecule is from 1:1 to 10:1.

2. The composition of claim 1, wherein the mass ratio of cationic clay to molecule is from 3:1 to 8:1.

3. The composition of claim 1, wherein the composition comprises from 5 to 30 wt % double stranded RNA.

4. The composition of claim 1, wherein the molecule comprising a plurality of positively charged groups is a polyalkyleneamine optionally substituted by one or more of alkyl, hydroxy, O-alkyl, —NH-alkyl or —N-(alkyl)-alkyl groups.

5. The composition of claim 1, wherein the molecule comprising a plurality of positively charged groups is a polymer which is or comprises poly(dialkylaminoalkylmethacrylate).

6. The composition of claim 1, wherein the composition is a topical composition.

7. The composition of claim 1, wherein the double stranded RNA is insecticidal double stranded RNA.

8. The composition of claim 7, wherein the insecticidal double stranded RNA is insecticidal to insects of the order *Diptera*, *Lepidoptera* or *Coleoptera*.

9. The composition of claim 1, wherein the composition is a plant-protecting composition.

10. The composition of claim 7, wherein the insecticidal double stranded RNA targets at least one of the group consisting of: the electron transport chain (ETC) of an insect, a voltage-dependent channel of an insect, a muscle of an insect, a gut of an insect, a body wall and/or appendages of an insect, an intracellular receptor of an insect, a GTPase hydrolase enzyme of an insect, a juvenile hormone esterase of an insect, the mitochondria of an insect, and the cuticle and/or epidermis of an insect.

11. The composition of claim 1, wherein the cationic clay is bentonite.

12. The composition of claim 1, wherein the molecule comprising a plurality of positively charged groups is a polymer having two or more positively charged nitrogen atoms.

13. The composition of claim 12, wherein the polymer is polyethylene-based, wherein the ethylene group in the polyethylene-based polymer is substituted by an amino group and optionally substituted by an electron withdrawing group vicinal to the amino group.

14. The composition of claim 12, wherein the ratio of nitrogen in the polymer to the phosphorous in the double stranded RNA is at least 4.

15. A preparation comprising the composition of claim 1, an aqueous phase and a solid phase; and wherein the preparation is sprayable onto a plant.

16. A method of delivering double stranded RNA to an insect having a basic pH within its alimentary canal, the method comprising administering the composition of claim 1 to an insect food.

17. The method of claim 16, wherein the insect food is a plant, a plant part, a synthetic insect food source, an insect bait or a water trap.

18. A method of protecting a crop against an insect having a basic pH within its alimentary canal, the method comprising the step of administering the composition of claim 1 to a crop.

19. The method of claim 18, wherein the composition is administered to the crop by spraying, drip-feeding or irrigation.

20. A method of preparing the composition of claim 1, the method comprising the steps of:
    a. adsorbing the double stranded RNA onto the molecule comprising a plurality of positively charged groups; and
    b. adsorbing the double stranded RNA/molecule onto the cationic clay.

21. A kit comprising:
    a. a clay complex; and
    b. double stranded RNA;
wherein the double stranded RNA is adsorbable onto the clay complex to form the composition of claim 1.

* * * * *

SEQUENCE LISTING

<160> NUMBER OF SEQ ID NOS: 22

<210> SEQ ID NO 1
<211> LENGTH: 300
<212> TYPE: DNA
<213> ORGANISM: Helicoverpa armigera

<400> SEQUENCE: 1

| | | | | | |
|---|---|---|---|---|---|
| cgcatacacc | agctgaaaag | gtgttggtgc | acccettgcc | aaaaacctcg | actgtggagt | 60 |
| cactgcatgg | atccctgcct | atccagggct | tgaaggccag | agtaaacggt | cgcgttttgt | 120 |
| taaatatttc | tggggattta | cgacgaaaaa | tcgtgttaca | taacaccttg | tcacttctag | 180 |
| ggccaagcca | tgtacgtttc | gcgcataccg | acatcagcta | ccccgacttc | tcggcgtacc | 240 |
| gtcgcaagga | gacgcaggat | cccacctcaa | gggctaacga | aacgtcgat | ggacgtcagt | 300 |

<210> SEQ ID NO 2
<211> LENGTH: 232
<212> TYPE: DNA
<213> ORGANISM: Helicoverpa armigera

<400> SEQUENCE: 2

| | | | | | |
|---|---|---|---|---|---|
| gcgctagacg | ccgacgcgtc | tctgcatgcc | aaggtcaaca | acaaatctct | cattggtctt | 60 |
| ggataccaac | agaagttgcg | cccaggcgtg | actttgacaa | tttctgctgc | tatcgatggc | 120 |
| cagaacttca | acgctggtgg | acacaaagtg | ggtgtcgccc | tggagctcga | gccctaagta | 180 |
| cacagaggcg | cttcggcttt | tagtcctgta | gataatacat | aatgccacac | tg | 232 |

<210> SEQ ID NO 3
<211> LENGTH: 339
<212> TYPE: DNA
<213> ORGANISM: Artificial Sequence
<220> FEATURE:
<223> OTHER INFORMATION: Green Fluorescent Protein

<400> SEQUENCE: 3

| | | | | | |
|---|---|---|---|---|---|
| aggacgacgg | caactacaag | acccgcgccg | aggtgaagtt | cgagggcgac | accctggtga | 60 |
| accgcatcga | gctgaagggc | atcgacttca | aggaggacgg | caacatcctg | ggcacaagc | 120 |
| tggagtacaa | ctacaacagc | cacaacgtct | atatcatggc | cgacaagcag | aagaacggca | 180 |
| tcaaggtgaa | cttcaagatc | cgccacaaca | tcgaggacgg | cagcgtgcag | ctcgccgacc | 240 |
| actaccagca | gaacacccccc | atcggcgacg | gccccgtgct | gctgcccgac | aaccactacc | 300 |
| tgagcaccca | gtccgccctg | agcaaagacc | ccaacgaga | | | 339 |

<210> SEQ ID NO 4
<211> LENGTH: 200
<212> TYPE: DNA
<213> ORGANISM: Helicoverpa armigera

<400> SEQUENCE: 4

| | | | | | |
|---|---|---|---|---|---|
| gatgacaggc | ttggtttcct | gactttctgc | cccaccaact | tgggaaccac | cgtgcgtgcc | 60 |
| tccgtgcaca | tcaagctgcc | caagctggct | gccgacaagg | ccaagctgga | ggagatcgca | 120 |
| tccaagtacc | acctgcaggt | gcgcggaacc | cgcggcgagc | acaccgaggc | tgagggcggc | 180 |
| gtctacgaca | tctccaacaa | | | | | 200 |

<210> SEQ ID NO 5
<211> LENGTH: 231
<212> TYPE: DNA
<213> ORGANISM: Helicoverpa armigera

<400> SEQUENCE: 5

```
ttccttgaat tcgaaattac tggctccacc tacgaaccca ttggtgacgt ttacctgaag    60
ggacagaaga tcaaggccgc tgaattcgat gctctgcacg aacttggtac catttgcgtt   120
atgtgcaatg actccgctat tgatttcaac gaattcaaac aggctttcga aaaggtcggt   180
gaggccactg aaaccgctct tatcgtcctc gctgagaaaa tgaacccctt c            231
```

<210> SEQ ID NO 6
<211> LENGTH: 300
<212> TYPE: DNA
<213> ORGANISM: Helicoverpa armigera

<400> SEQUENCE: 6

```
gaaagcagat gaggctctgc tcaagaagct ggaggaagct ctgcacttcc tcaacacatt    60
cctcgaaggt cagaagtacg ctgcgggtga caaactgacc ttggcagacc tcagtctcgt   120
ggcgactgtg tccactatag acgccgtcga catcagcctg aaggaatatc ccaatgttga   180
aaagtggttc gagctggtga agcgactgc cccgggatac caggaagcaa atgaagctgg   240
ccttaaagca ttcagagcta tggtagcgca gttaaaagct aaaactgaat tgtaagtgta   300
```

<210> SEQ ID NO 7
<211> LENGTH: 310
<212> TYPE: DNA
<213> ORGANISM: Helicoverpa armigera

<400> SEQUENCE: 7

```
gagtggagac tcaacgaaga tcaattggcc ggtgcacacg gcgtccgggc gtgaatacct    60
gtccttagca gtcaactcca gctccatagg ccacgggctg agggtcaagg agtgcgcctt   120
ctggcagaag tacttgccac agttgatggc tgccaccaat aagccagaac ctccgaagaa   180
ttgcacgaac agcgcagcgc ccgtcaaggt cccgtacgaa atcttcggcg tgggcgtcgt   240
gatagctacg ggcttagcca agacaacgtg gttcaagtac atcatatgag ttcattatgt   300
ggtctaagag                                                          310
```

<210> SEQ ID NO 8
<211> LENGTH: 309
<212> TYPE: DNA
<213> ORGANISM: Helicoverpa armigera

<400> SEQUENCE: 8

```
ccaccaagat ctacacggac cagaatattt ggtcagcaag aatgccatcg tcatcacatt    60
taattacaga ttgaacgtct tcggtttcct gtccatgaat acgacaaaaa tccccggcaa   120
cgctggtctc cgagaccagg tgaccctgtt gcgctgggtg cagagaaatg ctaagcattt   180
cggaggagac cccaacaacg tcaccatagc ggggcagagc gctggtgcag cagccgcgca   240
tctattgact ctgtctaaag ctgctaaagg tcttttcaaa agagcaatct tgatgagcgg   300
aacaggaat                                                           309
```

<210> SEQ ID NO 9
<211> LENGTH: 375
<212> TYPE: DNA
<213> ORGANISM: Helicoverpa armigera

<400> SEQUENCE: 9

```
gccgcataga tggcattcta aggcgttccg ataaagccac atcaaatggt gttcaggatg    60
```

```
agcaaattat aagaaggcaa agagtaagaa ctaatagaac attttcatcc agtgggaatg    120
atgttgtttt tattggtatg attcatgttc tatccagtgc aatgccacct cgaattctac    180
cccctacagc ctattcagaa tactggacga gacatttgat tgatggtcgt atcgttcagt    240
gtgaccagag tatatcatta gcaattggct acatgacaga agaagttact ggaacatctg    300
ctttcgtctt catgcacaaa gatgatgtcc gctgggtaat ttgtgtatta cgacaaatgt    360
atgatgagag ccggg                                                    375

<210> SEQ ID NO 10
<211> LENGTH: 313
<212> TYPE: DNA
<213> ORGANISM: Helicoverpa armigera

<400> SEQUENCE: 10
aggacatgga ggaatcaaga gaagtcactt ttacagaagc tagtcaatttt gcccaagaaa    60 atgaattgat gtttcttgaa accagtgcta aaacaggtga aaatgtagaa gaagcttttct   120 tgaaatgttc caaaacaatt ttggctaaaa ttgaaacagg tgaattagat cccgagcgaa    180
taggttcagg cattcaatat gggactggga cctctaaaag gcttagcgcg cccaagaaac    240
ctgcaagaag tccatctgat tgtgcttgtc atgtataaca ttatttcttg gatacataga    300
atgcatgatc tgc                                                      313

<210> SEQ ID NO 11
<211> LENGTH: 242
<212> TYPE: DNA
<213> ORGANISM: Helicoverpa armigera

<400> SEQUENCE: 11
acgattccgt tcgaacagac gttccgtgac ctctctgttc agagcaacga ccctcgccgc     60
cccaacttgg ccgagttcaa cttctgcggt tgcggctggc cccagcacat gttggtcccc    120
aagggtactg aggcgggcgc cgcctaccag ttgttcgtta tgcttttcgaa ctacgatctt   180 gacagcgtgg aacaacctga cggctcacag ttgagctgcg tcgaagcttc cagtttctgc    240
gg                                                                  242

<210> SEQ ID NO 12
<211> LENGTH: 280
<212> TYPE: DNA
<213> ORGANISM: Helicoverpa armigera

<400> SEQUENCE: 12
ggtggaggac aagttccgca tgaagatcta cctggagaac aagcaccgca tcgccaagca     60
caaccagcgc ttcgagcagg gcgccgtcag ctacaagctg cgccccaaca agtacgccga    120
catgctcagc cacgagttcg tgcacgtcat gaacggcttc aacaagaccc tcaagcaccc    180
gaaggccgtg cacggcaagg tcgcgagtc ccggcccgcc acgttcatcg cgccggcgca    240
cgtcacctac cccgaccacg tggactggcg caagaagggc                         280

<210> SEQ ID NO 13
<211> LENGTH: 374
<212> TYPE: DNA
<213> ORGANISM: Helicoverpa armigera

<400> SEQUENCE: 13
gccacaagcg tggtgccatg atcccactgc tcgacctggc tcagcgtcag gctggaggtt     60
ggctgccgat atctgccatg cataaagtag ctgaaatcct caaacttcct cgcatgagag    120
```

```
tttatgaggt tgctacgttc tacactatgt ttattagacg accaatcggc aagtaccata      180
tccaagtttg cacgacaact ccttgctggc tccgaggttc tgatgctatc ctgaaagctc      240
tcactgaggg tacacaatgc catgttggag gaaacagccc ttgtggcaag ttctctattt      300
ctgaggttga atgccttggt gcctgtgtta atgctcctat gattcaagtc aacgatgatt      360
actacgaaga cctg                                                        374

<210> SEQ ID NO 14
<211> LENGTH: 255
<212> TYPE: DNA
<213> ORGANISM: Helicoverpa armigera

<400> SEQUENCE: 14
ggttgaatgc cttggtgcct gtgttaatgc tcctatgatt caagtcaacg atgattacta      60
cgaagacctg tcagtagatg acacaaagga aattattgaa aagctcaaaa gggacgagaa      120
accgaaagct ggccctagga gcggcagatt cgcctcagaa cccttgggag gactcacttc      180
tctcaccgaa gaacctacag gccccggttt tggactacaa cccggcctca aggcctagaa      240
caaaaagttt ccgtt                                                       255

<210> SEQ ID NO 15
<211> LENGTH: 40
<212> TYPE: DNA
<213> ORGANISM: Artificial Sequence
<220> FEATURE:
<223> OTHER INFORMATION: Rieske primer 1

<400> SEQUENCE: 15
taatacgact cactataggg agtcggggta gctgatgtcg                            40

<210> SEQ ID NO 16
<211> LENGTH: 40
<212> TYPE: DNA
<213> ORGANISM: Artificial Sequence
<220> FEATURE:
<223> OTHER INFORMATION: Rieske primer 2

<400> SEQUENCE: 16
taatacgact cactataggg aggcaagttc atcggtggtt                            40

<210> SEQ ID NO 17
<211> LENGTH: 20
<212> TYPE: DNA
<213> ORGANISM: Artificial Sequence
<220> FEATURE:
<223> OTHER INFORMATION: Rieske primer 3

<400> SEQUENCE: 17
ccgcaaacga gattagcacc                                                  20

<210> SEQ ID NO 18
<211> LENGTH: 19
<212> TYPE: DNA
<213> ORGANISM: Artificial Sequence
<220> FEATURE:
<223> OTHER INFORMATION: Rieske primer 4

<400> SEQUENCE: 18
acttcggcgg ctactactg                                                   19

<210> SEQ ID NO 19
```

```
<211> LENGTH: 21
<212> TYPE: DNA
<213> ORGANISM: Artificial Sequence
<220> FEATURE:
<223> OTHER INFORMATION: VDAC primer 1

<400> SEQUENCE: 19
gactgcggta ttagcatgaa g                                      21

<210> SEQ ID NO 20
<211> LENGTH: 22
<212> TYPE: DNA
<213> ORGANISM: Artificial Sequence
<220> FEATURE:
<223> OTHER INFORMATION: VDAC primer 2

<400> SEQUENCE: 20
cagagaacac ttgaagatac tg                                     22

<210> SEQ ID NO 21
<211> LENGTH: 21
<212> TYPE: DNA
<213> ORGANISM: Artificial Sequence
<220> FEATURE:
<223> OTHER INFORMATION: RPL primer

<400> SEQUENCE: 21
acaggtatcc ccgcaaagtg c                                      21

<210> SEQ ID NO 22
<211> LENGTH: 21
<212> TYPE: DNA
<213> ORGANISM: Artificial Sequence
<220> FEATURE:
<223> OTHER INFORMATION: RPLS27 primer

<400> SEQUENCE: 22
gtccttggcg ctgaacttct c                                      21
```